United States Patent [19]

Hiramatsu et al.

[11] Patent Number: 6,156,507
[45] Date of Patent: Dec. 5, 2000

[54] **METHOD OF IDENTIFYING METHICILLIN-RESISTANT *STAPHYLOCOCCUS AUREUS* OR METHICILLIN-RESISTANT COAGULASE-NEGATIVE STAPHYLOCOCCI**

[75] Inventors: Keiichi Hiramatsu, Tokyo; Teruyo Ito, Kawaguchi; Akira Awaya, Yokohama; Hiroie Ohno, Tokyo; Tsukasa Hayashi, Itoh, all of Japan

[73] Assignee: Kainos Laboratories, Inc., Tokyo, Japan

[21] Appl. No.: 08/945,810

[22] PCT Filed: Feb. 21, 1997

[86] PCT No.: PCT/JP97/00487

§ 371 Date: Oct. 23, 1997

§ 102(e) Date: Oct. 23, 1997

[87] PCT Pub. No.: WO97/31125

PCT Pub. Date: Aug. 28, 1997

[30] Foreign Application Priority Data

Feb. 23, 1996 [JP] Japan .................................. 8-060373

[51] Int. Cl.[7] .............................. C12Q 1/68; C12P 19/34; C07H 21/04
[52] U.S. Cl. ......................... 435/6; 435/91.2; 435/91.21; 435/91.5; 435/91.51; 536/23.7; 536/24.33; 536/24.32
[58] Field of Search .............................. 435/6, 91.2, 91.5, 435/91.21, 91.51; 536/23.7, 24.33, 24.32

[56] References Cited

U.S. PATENT DOCUMENTS 5,702,895  12/1997  Mtsunaga et al. .......................... 435/6

OTHER PUBLICATIONS

Hiramatsu et al. FEBS. 298:133–136, Feb. 1992.
Archer et al. Antimicrobial Agents and Chemotherapy. 38:447–454, Mar. 1994.
Barberis–Maino et al. Gene. 59:107–113, 1987.

*Primary Examiner*—Carla J. Myers
*Attorney, Agent, or Firm*—Knobbe, Martens, Olson & Bear, LLP

[57] ABSTRACT

Disclosed is a specific identification method of an MRSA and MRC-NS, which is speedy, simple and reliable. Specifically, the present invention provides a diagnostic method of an MRSA or MRC-NS, which comprises performing a reaction with a sample by making combined use of a part of a mecDNA, which is an integrated adventitious DNA existing on a chromosome of the MRSA or MRC-NS and carrying an mecA gene thereon, and a part of a nucleotide sequence of a chromosomal DNA surrounding the integrated DNA; and also a diagnostic method of an MRSA or MRC-NS by PCR, LCR or hybridization, which comprises performing a reaction with a sample by using a nucleotide sequence of a chromosomal DNA surrounding an integrated site of a mecDNA in a chromosome of an MSSA or MSC-NS, wherein said method makes use of an occurrence of a negative reaction when said sample contains a mecDNA integrated therein.

16 Claims, 27 Drawing Sheets

OUTLINE OF MRSA IDENTIFICATION METHOD BY PCR
WHICH MAKES USE OF NUCLEOTIDE SEQUENCES OF
mec REGION DNA, intM AND ITS UPSTREAM REGION

A MRSA

B MSSA

C MR staphylococci (Strain other than S. aureus)

RESTRICTION MAPPING OF LD8325, INCLUDING mec
INTEGRATION SITE, AND PARTIAL SEQUENCE THEREOF
source: NCTC8325

```
  H        E    P    H    H    S
  |--------|----|----|----|----|  Kb
  1   3.2    3.2  1.4  2.4   5.4
              →
           pLEC12(pLEC1a)
```

```
ctgcagaggt aattattcca aacaatacca ttgatttcaa aggagaaaga gatgacgtta    60
gaacgcgtga aacaaattta ggaaacgcga ttgcagatgc tatggaagcg tatggcgtta   120
agaatttctc taaaaagact gactttgccg tgacaaatgg tggaggtatt cgtgcctcta   180
tcgcaaaagg taggtgaca cgctatgatt taatctcagt attaccattt ggaaatacga   240
ttgcgcaaat tgatgtgaaa ggttcagacg tctggacggc tttcgaacat agtttaggcg   300
caccaacaac acaaaaggac ggtaagacag tgttaacagc gaatggcggt ttactacata   360
tctctgattc aatccgtgtt tactatgata taaataaacc gtctggcaaa cgaattaatg   420
ctattcaaat tttaaataaa gagacaggta agtttgaaaa tattgattta aaacgtgtat   480
atcacgtaac gatgaatgac ttcacagcat caggtggcga cggatatagt atgttcggtg   540
gtcctagaga agaggtatt tcattagatc aagtactagc aagttattta aaaacagcta   600
acttagctac gtatgatacg acagaaccac aacgtatgtt attaggtaaa ccagcagtaa   660
gtgaacaaacc agctaaagga caacaaggta gcaaaggtag taagtctggt aaagatacac   720
aaccaattgg tgacgacaaa gtgatggatc cagcgaaaaa accagctcca ggtaaagttg   780
ttttgttgct agcgcataga ggaactgtta gtagcggtac agaaggttct ggtcgcacaa   840
tagaaggagc tactgtatca agcagagtg ggaaacaatt ggctagaatg tcagtgccta   900
aggtagcgc tactgagaaa cagttaccaa aaactggaac taatcaaagt tcaagcccag   960
aagcgatgtt tgtattatta gcaggtatag gtttaatcgc gactgtacga cgtagaaaag  1020
ctagctaaaa tatattgaaa ataatactac tgtatttctt aaataagagg tacgtagtg  1080
ttttttatg aaaaaaagcg ataaccgttg ataaatatgg gatataaaaa cgaggataag  1140
taataagaca tcaaggtgtt tatccacaga aatgcccaca gagttaccag gttatccaga  1200
atttaaagag aatacccac aatgcccaca tcaaaaactg caaatacaca ggttatacac  1260
taaaaatcgg gcataatgt caggaaaata tcaaaaactg tgtggataac gttaacaatg  1320
agaggaaca gtgtgaacaa gttaataact tgtggataac tggaagttg ataacaattt  1380
```

NUCLEOTIDE SEQUENCE OF CHROMOSOMAL DNA's
FLANKING mec INTERGRATION SITE AS COMPARED AMONG MSSA STRAINS

```
25923   1: TTCGTCATTGGCGGATCAAACGCGGCCTGCACAAGGACGTCTTCACACGCAGTAACTACGCA  60
STP23   1: TTCGTCATTGGCGGATCAAACGCGGCCTGCACAAGGACGTCTTCACACGCAGTAACTACGCA  60
8325    1: TTCGTCATTGGCGGATCAAACGCGGCCTGCACAAGGACGTCTTCACACGCAGTAACTACGCA  60
STP43   1: TTCGTCATTGGCGGATCAAACGCGGCCTGCACAAGGACGTCTTCACACGCAGTAACTACGCA  60
STP53   1: TTCGTCATTGGCGGATCAAACGCGGCCTGCACAAGGACGTCTTCACACGCAGTAACTACGCA  60

25923  61: CTATCATTCAGCAAAATGACATTCCCACACATCAAATGATGCGGGTTGTGTTAATTGAACAA 120
STP23  61: CTATCATTCAGCAAAATGACATTCCCACACATCAAATGATGCGGGTTGTGTTAATTGAACAA 120
8325   61: CTATCATTCAGCAAAATGACATTCCCACACATCAAATGATGCGGGTTGTGTTAATTGAACAA 120
STP43  61: CTATCATTCAGCAAAATGACATTCCCACACATCAAATGATGCGGGTTGTGTTAATTGAACAA 120
STP53  61: CTATCATTCAGCAAAATGACATTCCCACACATCAAATGATGCGGGTTGTGTTAATTGAACAA 120

25923 121: GTGTACAGAGCATTTAAGATTATGCGTGGAGAGGCGTATCACACAAATAAAAACT--AAAAA- 177
STP23 121: GTGTACAGAGCATTTAAGATTATGCGTGGAGAGGCGTATCACACAAATAAAAACT--AAAAA- 177
8325  121: GTGTACAGAGCATTTAAGATTATGCGTGGAGAGGCGTATCACACAAATAAAAACTAAAAAAT- 179
STP43 121: GTGTACAGAGCATTTAAGATTATGCGTGGAGAGGCGTAT---C--AT---AAGT----AA--- 168
STP53 121: GTGTACAGAGCATTTAAGATTATGCGTGGAGAGGCGTATC----A--T---AAGT-----GATG 170

25923 178: ---TG---AG-T-A--ACTATT-A-AT-A--T--AG--T-----A-TAAATTCAATA--T-- 211
STP23 178: ---TG---AG-T-A--ACTATT-A-AT-A--T--AG--T-----A-TAAATTCAATA--T-- 211
8325  180: -TCTGTATGAC--GA-GA----T--A-ATAATTTGGAG-----G--GT--GTT-AA-A--T- 216
STP43 169: ---TG-A-G-GTTCATGATTTTTTGACAT-AGTT--AGCCTCCGCAGT-CTTTC-A-A---- 213
STP53 171: CT-TGT-T-AG----AATGA--TTTTA-ACAA--T---A-----T-----G-A-----AATAGCT 205
```

FIG. 5A

```
25923  212:  G-GTGATA-A--AA-A-CA----G      225
STP23  212:  G-GTGATA-A--AA-A-CA----G      225
8325   217:  G-GTG-------GA-CA----T        225
STP43  214:  --GT-A-A-AT-AATATC----        225
STP53  206:  GTG-GA-AGCTCAA-A-CATTGT       225
```

FIG. 5B

NUCLEOTIDE SEQUENCE OF CHROMOSOME REGION CONTAINING
DOWNSTREAM JUNCTION OF mec: COMPARISON BETWEEN MRSA
AND METHICILLIN-RESISTANT s. haemolyticus, s. epidermidis N315    1: CTCATTACTTATGATAAGCTTCTTAAAACATAACAGCAATTCACATAAACCTCATATGT    60
SE G3   1: CTCATTACTTATGATAAGCTTCTTAAAACATAACAGCAATTCACATAAACCTCATATGT    60
SH 518  1: CTCATTACTTATGATAAGCTTCTTAAAACATAACAGCAATTCACATAAACCTCATATGT    60
SH JA178 1: CTCATTACTTATGATAAGCTTCTTAAAACATAACAGCAATTCACATAAACCTCATATGT   60

N315    61: TCTGATACATTCCAAATCCCTTTATGAAGCGGCTGAAAAAACCGCATCATTTATGATATG  120
SE G3   61: TCTGATACATTCAAAATCCCTTTATGAAGCGGCTGAAAAAACCGCATCATTTATGATATG  120
SH 518  61: TCTGATACATTCAAAATCCCTTTATGAAGCGGCTGAAAAAACCGCATCATTTATGATATG  120
SH JA178 61: TCTGATACATTCAAAATCCCTTTATGAAGCGGCTGAAAAAACCGCATCATTTATGATATG 120

←— intMN315
                          mec →
N315    121: CTTCT--CC-A-C------GC---ATAA-TCTTAAATGCTCTATACACTTGCTCAATT    164
SE G3   121: CTTC-GCCCTCTCA-TGA---T-C-----TTAAATGCCGGATAAATTTGTTCGA--T   163
SH 518  121: CTTC--CCT--C-------GC---ATGA-TTTTAAATGCTCTGTATACTTGCTCGATT   163
SH JA178 121: CTTCTCCCTATCAGTGATTTTGCTAAAAAATTTTAAA-G-T-TAT-TA-TT-T----TT 170

N315    165: AAC-ACA--ACCCGCATCA-TTT-GATGTGG---GAATGTCATT--T-TGCTGAA--TGA  211
SE G3   164: --CAATATGACCCGCAT-A-TTT-GGTGTGG---GAAGGTCA--T---AT-TGCT-A---A  207
SH 518  164: AAG-ACA--ACCCGCATCA-TTT-GATGTGG---GAATGTCA--T---T-T---T-AC-TGA 206
SH JA178 171: -TCAACA--A----AT-ACTTTAGA-G-GGTTTTAT-T-ATTAAATAT--T-AACTTTA  214

*FIG. 6A*

```
N315    212:  --T-AGTGCGT--AG------TTACTGCGTTG-TAA-GA-CGTCCTTGTGCAG-G----CC     253
SE G3   208:  ---AA---G-ATAAAGCATAGTTGCTGCGTTG-TAA-GA-CGT-C-T-TG--GTGTAAACC     253
SH 518  207:  ATGAAA-----GTGCGTAGTTGCTGCGTTG-TAA-GA-CGTCCTCATGC-----AATCC     252
SH JA178 215: TTTAAAT-TTTAAAGTCTTTTTAAT--ATTGATAANGATC-TCCCTAT---A-------     259

N315    254:  GTTTGATCCGCCAATGACGAATACAAAGTCGCTTTGCCCTTGGGTCATGCGTTGGTT--CAA   313
SE G3   254:  ATTGGAGCCACCTATGACAAATGTAAAGTCGCTTTGACCTTGTGTCATGCG-TGTTTGTAG   313
SH 518  253:  ATTTGATC                                                         260
SH JA178 260: G---TG                                                           262

N315    314:  TTCTTGGGCCAATCCTTCGGAAGA
SE G3   314:  TTCTTTAGCGAGTCCTTCTGAAGA
```

FIG. 6B

```
  1'  gaattcgatagttttttagcaataaagtatctaatacttctatttattcaagtctttt
       ************************************************************
  1"  gaattcgatagttttttagcaataaagtatctaatacttctatttattcaagtctttt 61'  aaagttactattctaggaaattcactaatttttgaggaagattaataatagcgtttatt
       ************************************************************
 61"  aaagttactattctaggaaattcactaatttttgaggaagattaataatagcgtttatt 121'  tctttgattatcacactaatttatctatgaattgctgctttctattcggtacacgcaat
       ************************************************************
121"  tctttgattatcacactaatttatctatgaattgctgctttctattcggtacacgcaat 181'  gaaatacttgtaccacaagtcattgttttccaaaaatttgaggattctgtggatgtcct
       ************************************************************
181"  gaaatacttgtaccacaagtcatcgtttttccaaaaatttgaggattctgtggatgtcct 241'  tggactgatataagattctgaaggtctaacgtaatctacactattccttctataatta
       ************************************************************
241"  tggactgatataagattctgaaggtctaacgtaatctacactattccttctataatta 301'  acaatctctttaagcctgttttgttgaaaaattaacattttattaactatgtcttca
       ************************************************************
301"  acaatctctttaagcctgttttgttgaaaaattaacattttattaactatgtcttca 361'  tttttgattgctctttctgcaaatcaattccgaagtcataatcaaatatttata
       ************************************************************
361"  tttttgattgctctttctgcaaatcaattccgaagtcataatcaatcaaatatttata
```

FIG. 9A

```
421'  tcatgatatgcttgtcccaaaagtataatatatacattatttgtaatgtagtatcttct
      ************************************************************
421"  tcatgatatgcttgtccaaaagtataatatatacattatttgtaatgtagtatcttct 481'  ttgagaaataatattgcatcaaaatgatgaccggattctgaaaataaattgtcatcttct
      ************************************************************
481"  ttgagaaataatattgcatcaaaatgatgaccggattctgaaaataaattgtcatcttct 541'  tcagtatctaggtatacattcttattaataattgccaatctaatagttttttgtctttt
      ************************************************************
541"  tcagtatctaggtatacattcttattaataattgccaatctaatagttttttgtctttt 601'  ttacgtatataaactttactaatttaattcattgaatcactaacaagttcttta
      ************************************************************
601"  ttacgtatataaactttactaatttaattcattgaatcactaacaagttcttta 661'  tcattaagcagttcataattgtcatcattaaagattctagattctctaaaaatttgta
      ************************************************************
661"  tcattaagcagttcataattgtcatcattaaagattctagattctctaaaaatttgta 721'  tttgtttcctgaaattataaatagattataataatcttcatattacacccctta
      ************************************************************
721"  tttgtttcctgaaattataaatagattataataatcttcatattacacccctta 781'  attatatttacatctatttccattattacatttatgagtctcgcaaattgtcagtttt
      ************************************************************
781"  attatatttacatctatttccattattacatttatgagtctcgcaaattgtcagtttt 841'  taaattatgataattatttccaaatagtttattaaaaactacatcttttctgattgat
      ************************************************************
841"  taaattatgataattatttccaaatagtttattaaaaactacatctttctgattgat
```

FIG. 9B

```
 901'  actctttcaaatcttaataaaattctttgacccttattattacattctcaatttcttgga
       ************************************************************
 901"  actctttcaaatcttaataaaattctttgacccttattattacattctcaatttcttgga 961'  attgtctttgaaacttcattggaatattactatttttgtcaatatctgtaattta
       ******************************************************
 961"  attgtctttgaaacttcattggtatattactatttttgtcaatatctgtaattta 1021'  tttatgattattatcattacttagctacgtcaatgactgttgattatgaataactgtt
       *********************************************************
1021"  tttatgattattatcattacttagctacgtcaatgactgttgattatgaataactgtt 1081'  tctattgcaaagttacttttataattaataaggacaaaaagaagcattctatattaatc
       **********************************************************
1081"  tctattgcaaagttacttttataattaataaggacaaaaagaagcattctatattaatc 1141'  attttagatataaaccaatttgtgatataatcttcaactgttagctactacttaagtt
       *********************************************************
1141"  attttagatataaaccaatttgtgatagggcctaattcaactgttagctactacttaagtt 1141"  attttagatataaaccaatttgtgatagggcctaattcaactgttagctactacttaagtt 1201'  atatgcgcaattatcgtgatatctttatatattgaatgaacgtggattaatgtccacc
       *********************************************************
1201"  atatgcgcaattatcgtgatatctttatatattgaatgaacgtggattaatgtccacc 1261'  atttaacaccctccaaattattatctcctcatacagaatttttagttttacttatgata
       ***********************************************************
1261"  atttaacaccctccaaattattatctcctcatacagaatttttagttttacttatgata
              ←mec 1321'  cgcctctcctcgcataatcttaaatgctctgtacacttgttcaattaacacaacccgcat
       *******   *  * **    *****  *
1321"  cgcctct---gcgtatcagttaatg--atg-aggttttttaattgtcctt------t
```

FIG. 10A

```
1381'  catttgatgtgggaatgtcatttgctgaatgatagtgcgtagttactgcgttgtaagac
       ****   *   ***   **   *   ** ****   *   ** ****   *   *
1367"  aattt--ttcttcaat--ca-aaggctccactcctct-attaatta-aacctttaattaa 1441'  gtccttgtgcaggccgtttgatccgccaatgacgaaacaaagtcgtttgccct-tggg
        *****  *    *  * *      ***   *   *     *
1420"  gt-cttgtgccgaaaatct-at---ttacagac-caagcaacataattagcactctagc 1500'  tcatgcgttggttcaattcttgggccaatcctcggaagatagcatctttccttgtattt
        *   ***   *       *   *            **   *   *  **
1474'  tgctg-tttcattcactcctataactgaagttattacataaatcatatatgctaatttag 1560'  ctaatgta---atgactgtgga-ttgtggtttgatttggctagtattcgttggccttct
          *    *   *   **   *  * *     * **   *   *     *
1533"  caaaggatcgtagtcttcaaacttccacaaacttgatactttctattaatactct 1616'  -tttctttactgctcaa------tttctttg----tcactca-tattttctggtgct
        *    *  * ****          *  ***   *    *  *     **
1593"  ctattaaatcacatgctgaagattcgttttttttgcatataacgaattaaacacgcttgc
                                                                  t 1664'  ttttcgt-ctggaacttctatgatgtctatcttggtgtatggcctaaacgt-ttttcat
        ** * ******  *  *   *  * *   **   *  *       * *   *
1653"  cattattattagaacttagaacattgacataattgttcatcacttcgtgtcataataa 1722'  attctgctatggcttgcttccaatattctctttt-ag--tttccctacagctaaaatgg
       *****  *  *  **  *  *  * *****     ****     *
1713"  attcttcgctttcat-catcaaacactcctctttttcagctttttcttgacattttcgacg 1779'  tgatttcatgtcgtttggtcctccaaattgttatcaacttccagttatccacaagtta
        ** *  * *   *  * **  *
1772"  tgctttgcag-tactgtgatactctaaattctctgcag
```

*FIG. 10B*

NUCLEOTIDE SEQUENCE HOMOLOGY BETWEEN pLEC12rc AND N314J3rc

```
1201'  atatgcgcaattatcgtgatatatcttatatattgaatgaacgtgatttaatgtccacc
  1"                                                          tatg
1261'  atttaacaccctccaaattattatctccctcatacagaatttttagttttacttatgata
       * * * *  *******            *    *   * *  * *********
  5"   ttctgatacattccaaatcccttatgaagcggctgaa-aaaaccgcatcatttatgata
       ** ***** *************************** ***********************
1321'  cgcctcctcgcataatcttaaatgctctgtacacttgttcaattaacacaacccgcat
       ** ***** **************************************************
 64"   tgcttctccacgcataatcttaaatgctctatacacttgctcaattaacacaacccgcat
        mec
1381'  catttgatgtgggaatgtcatttgctgaatgatagtgcgtagttactgcgttgtaagac
       ************************************************************
124"   catttgatgtgggaatgtcatttgctgaatgatagtgcgtagttactgcgttgtaagac
       ************************************************************
1441'  gtccttgtgcaggccgtttgatccgccaatgacgaaacaaagtcgctttgcccttgggt
       ********************************************************  *
184"   gtccttgtgcaggccgtttgatccgccaatgacgaatacaaagtcgctttgcccttg
```

FIG. 11

COMPARISON IN NUCLEOTIDE SEQUENCE
BETWEEN pSJB-2a OF N315 AND LO2C4 OF NCTC10442

```
961'   attgttctttgaaacttcattggtatattactattttttgtcaatatctgtaattta
                                                  ****************
  1"                                              atctgtaatttta 1021'  tttatgattattatcattacttagctacgtcaatgactgttgattatgaaataactgtt
       ********************************************************
 14"   tttatgattattatcattacttagctacgtcaatgactgttgattatgaaataactgtt 1081'  tctattgcaaagttactttataatttaataaggacaaaaagaagcattctatattaatc
       ********************************************************
 74"   tctattgcaaagttactttataatttaataaggacaaaaagaagcattctatattaatc 1141'  atttagatataaaccaatttgataggcctaatttcaactgttagctactacttaagtt
       ********************************************************
134"   attttagatataaaccaatttgataggcctaatttcaactgttagctactacttaagtt 1201'  atatgcgaattatcgtgatatatcttatatattgaatgaacgtggatttaatgtccacc
       ********************************************************
 94"   atatgcgcaattatcgtgatatatcttatatattgaatgaacgtggatttaatgtccacc 1261'  atttaacacccctccaaattattatctcctcatacagaattttttagttttactatgata
       ********************************************************
254"   atttaacacccctccaaattattatctcctcatacagaattttttagttttactatgata
          mec →

1321'  cgcctctgcgtatcagtaatgatgaggtttt-ttaattgtcctttaat--ttttcttc
       ******************* *********   *    *  *  ***
314"   cgcctctgcgtatcagataatgatgcggttttttaattattgataaggattgccatactta
```

FIG. 12A

```
1378'  aatcaa-aggc-tccactcctctat--taattaaacctt---aattaagtcttgtgccga
          *** *    *    ******   *    ***    **   ***   ** * * ***  *
 372"  ttacaatactcatagaagcctctcttgatacatatagattgcctttcaatatttcttta 1432'  aaatctatttacagaccaagcaacat-aatttagc--actct--agctgctgtttcattc
          *** *                *    *  **  **
 434"  ctatcaaattcaagtccttaaaatgagttcggcaaactctaatgctgccgttccatt- 1487'  actctataactgaagttattacataaaatcatatatgctaatttagcaaaaggatcgtag
          *  ****  *   *       *    *   ***       *         *     *
 493"  -agcagtaactaaattcgatctttttctgtaattcaacaaatttatgctttaacaa 1547'  tcttcaaaccttccacaaaactcttgatactttctattaatactctctattaaatcacat
           *   *     *      ***     *     * *      **
 552"  ctttaaaaagacaatttcactattgagctcttagatt-ataagttc-agtagcacaaat 1607'  gctgaagattcgtttttgcatataacgaattaaaacacgcttgctcattattattagaa
          **    * **  *        *  * * *** *   **  * * * *     ****  *
 610"  tgcaaatgctctatctaattc-tgtgactgttttaata-aaacgttaacatttatcctca 1667'  cttagaaccatttga-cataattgttcatca-cttcgtgtcataataat-tcttcgctt
          **  *       ** *****        * **   * **  * *** * **
 668"  cttaactctatcacatcataattcattaacagattgacgaacttatctgtgtctatgatt 1724'  tcatcatcaaacactcctctttcagctttcttgacattttcgacattttcgacgtgctttgcacta
          ** * *     *    ** *  ***    *  * * *  *
 728"  gtattgtgatttatccaagttttatattttaagcccttcttcttccaagctt
```

FIG. 12B

COMPARISON IN NUCLEOTIDE SEQUENCE
BETWEEN N315J3rc AND NCTC10442J3rc

```
  1'                                                            tatgttctgatac
 61" tgcttcactataagtattcagtatagagaatatttgctatattacttgaaatgaaag
                                                      mec →
 14' attccaaatcccttatgaagcggctgaaaaaaccgcatcatttatgatatgcttctcca
     ****  ****  **** * ****************************************
121' actgcggaggctaactatgtcaaaatcatgaacctcattacttatgataagcttctcct
 74' cgcataatcttaaatgctctatacacttgctcaattaacacaacccgcatcatttgatgt
     ************ ***** ******************************************
181" cgcataatcttaaatgctctgtacacttgttcaattaacacaacccgcatcatttgatgt
134' gggaatgtcatttgctgaatgatagtgcgtagtgctgcgttgtaagacgtccttgtgc
     ************************************************************
241" gggaatgtcatttgctgaatgatagtgcgtagtgctgcgttgtaagacgtccttgtgc
194' aggccgtttgatccgccaatgacgaatacaaagtcgctttgcccttg
     ***************************************  ******
301" aggccgtttgatccgccaatgacgaaaacaaagtcgcttt
```

FIG. 13

NUCLEOTIDE SEQUENCE N315IS-J3 OF N315mec CONTAINS NUCLEOTIDE
SEQUENCE OF mec DOWNSTREAM END REGION LOCATED ADJACENT
TO mec DOWNSTREAM JUNCTION OF NCTC 10442

```
1921'  tcaatatgtacttattatatttaccgtaatttactatatttagttgcagaaagaatttc
                      *********************************************
   1"            atattttaccgtaatttactatatttagttgcagaaagaatttc 1981'  tctcaaagctagaacttgcttcactataagtattcagtataagaatatttcgctatta
       **   *************************************************
  44"  tctccaagctagaacttgcttcactataagtattcagtatagagaatatttcgctatta 2041'  tttacttgaaatgaaagactgcggaggctaactatgtcaaaaatcatgaacctcattact
       ************************************************************
 104"  tttacttgaaatgaaagactgcggaggctaactatgtcaaaaatcatgaacctcattact 2101'  tatgataagcttcttaaaaacataacagcaattcacataaacctcatatgttctgataca
       ***************
 164"  tatgataagcttc
```

FIG. 14

COMPARISON BETWEEN NUCLEOTIDE SEQUENCE N315J3rc CONTAINING
DOWNSTREAM JUNCTION OF N315mec AND NUCLEOTIDE SEQUENCE pSJ10-3J3rc
CONTAINING mec DOWNSTREAM JUNCTION OF 85/3907

```
  1'                                                             tatgttctgata
 61"   acatcgtatgatattgcaaggtataatccaatatttcatatatgtaattcctccacatct
 13'   cattccaaatcccttatgaagcggctgaaaaaaccgcatcatttatgatatgcttctcc
       * **************************************** ******
121"   cattaaattttaaattatacacaacctaattttagtttattatgatacgcttctcc
                                                    mec
 73'   acgcataatcttaaatgctctatacacttgctcaattaacacacaacccgcatcatttgatg
       **************************************************** ******
181"   acgcataatcttaaatgctctgtacacttgttcaattaacacacaacccgcatcatttgatg
133'   tgggaatgtcatttgctgaatgatagtgcgtagttactgcgttgtaagacgtccttgtg
       **** *********************************************** ******
241"   tggggatgtcatttgctgaatgatagtgcgtagttactgcgttgtaagacgtccttgtg
193'   caggccgtttgatccgccaatgacgaatacaaagtcgctttgcccttg
       ****************************************
301"   caggccgtttgatccgccaatgacgaa
```

FIG. 15

COMPARISON BETWEEN NUCLEOTIDE SEQUENCE pSJ8-2a CONTAINING
UPSTREAM mec JUNCTION OF N315 AND NUCLEOTIDE SEQUENCE
LG12H2 CONTAINING UPSTREAM mec JUNCTION OF 85/3907

```
 961'  attgttcttttgaaacttcattgtatattactatttttgtcaatatctgtaatttta
                                              ***  ***    *** ***
   1"                                             gtcaactta 1021'  t-ttatgattattatcattacttagctacg-tcaatgactgttgattatgaaataactg
         *  **  ***      ***  *  **    *   *    ***
  10"  tcagctaattctttataatagctaaccacgttttatctatacacttcatcacaatatcc 1079'  tttctattgcaaagttactttatattaataaggacaaaagaagcattctatattaa
         **  *   * *  **      * ****  * ** * ** *
  70"  cctccgttg-taattacaatgtattatggaaagatagaaaatactacttttcaa-aatta 1139'  tcatttagatataaaccaat-ttgataggcctaatttcaactgttagctactacttaa
       *  *  * * *  ****   *  * *     *   *  *     *
 128"  tcccccttgcaaataaattttctataaatctattagtttactagattaataaatttcaat 1198'  gt-tatatgcgca-attatcgtgatatcttatatattgaatgaac-gtggattaatg
        * **   * *    *  ** **  *  *  ***
 188"  gtcgctaagtgcatttattctgt-tattatttaatttgaaaaacctgcttaaataatg 1255'  tccaccattta-----acacccctccaaattattatctcctcatacagaattttttagttt
        *     * *  *  ** *   ****  *
 247"  ataatcacttacataaacatcgtactttatgataagtcacaaggtaaaaactcctccgc
                      ┌─ mec 1310'  tacttatgatacgcctctgcgtatcagttaatgatgaggttttttaattgtcctttaat
       **************** ** ******   ***  *  *
 307"  tacttatgatacgcttctgcttatcagttgatgatgcgg--ttttaa--gt--aataa-
```

FIG. 16A

```
1370'  ttttcttcaatcaaaggctccactcctctattaataacctttaattaagt---cttgt
       * ** *****  ***      **  * *** *** *           ****  *  ** *
 360"  gt-tcatcaaaaaataattggcttat-tatgaacaactaacagaattgattccaattat 1427'  gccgaaatctatttacagaccaagcaacataatttagcactctagctgctgtttcattc
       * ****** *             *         * * ***   *  *  * ****
 418"  actactcacaatttatatagtaatcttcaatagatatgattttaattttaaattatta 1487'  act-ctataactgaagttattacataaaatcat-atatgctaatttagc--aaaaggatc
       *** * * **  *  *             **  *      *  *   ** *
 478"  actacaatcacctca--taataatggctttcttcgcctgttaattacctacatagaaag 1543'  gtagtcttcaaaccttccacaaaactcttgatactttctattaatactctctattaaatc
        * ***  *  ****     *
 536"  ctggtgttccttttttacttttacccgt
```

FIG. 16B

NUCLEOTIDE SEQUENCE OF N315IS-J3

```
atctcttcaa   tttatttta    tatgaatcct   gtgactcaat   gattgtaata   tctaaagatt    60
tcagttcatc   atagacaatg   ttcttttcaa   catttttat    agcaaattga   ttaaataaat   120
tctctaattt   ctcccgtttg   atttcactac   catagattat   attatcattg   atatagtcaa   180
tgaataatga   caattatca    ctcataacag   tcccaacccc   tttgttttga   tagactaatt   240
atcttcatca   ttgtaaaaca   aattacaccg   tttaaattta   actcaactta   aatatcgaca   300
aattaaaaaa   caataaaatt   acttgaatat   tattcataat   atattaacaa   ctttattata   360
ctgctcttta   tatataaaat   cattaataat   taaacaagcc   ttaaaatatt   taacttttt   420
gtgattatta   cacattatct   tatctgctct   ttatcaccat   aaaaatagaa   aaaacaagat   480
tcctaaagaa   tataggaatc   ttgtttcaga   ctgtggacaa   actgattttt   tatcagttag   540
cttatttaga   aagtttatt   taaattacag   tttctatttt   tattagatca   caattttatt   600
ttagctcttg   ttcaagtaat   cattttttcgc   caaaaacttc   atactgaata   gcttctacat   660
taaatacttt   gtcaatgaga   tcatctacat   cttaaattc   agaataattt   gcatatggat   720
ctataaaata   aaattgtggt   tcttttaccgg   aaacattaaa   tattcttaat   attaaatatt   780
tctgcttata   ttctttcata   gcaaacattt   catttagcga   cataaaaat   ggttcctcaa   840
tactagaaga   tgtagatgtt   ttaatttcaa   taaatttttc   tacagcttta   tctgtatttg   900
ttggatcaaa   agctactaaa   tcatagccat   gaccgtgttg   agagcctgga   ttatcattta   960
aaatattcct   aaactgttct   ttcttatctt   cgtctatttt   attatcaatt   agctcattaa  1020
agtaatttag   cgctaatttt   tctccaactt   taccggttaa   ttgatacacc   ttatttgatt  1080
tttcaatttc   tgaatcattt   ttagtagtct   tctttatcttt   tttttatat   tttgaatta  1140
ttcctttagg   tgcttccact   tctttgagtg   tcttatcttt   ttgtgctgtt   ctaatttctt  1200
caatttcgct   gtcttcctgt   atatcgtcta   tgctattgac   caagctatca   taggatgttt  1260
ttgtaacttt   tgaagctaat   tcattaaata   tcattcaaat   gttctaaaaa   tcctctagca  1320
tatcttcttc   tgtgaatcct   tgtgataatca   tcattcaaat   catatattt   gatccatgag  1380
aatatcctga   tggataatca   ttttttaaat   catagatga   atctttatt   tctgcgtaat  1440
aaaatcttcc   agtattaaat   tcatttgatg   tcatatatt   attgagttcg   gaagtaaag  1500
ttaatgctct   ttgttttgca   gcattttat   ccgcggaaa   catatcactt   atctttgacc  1560
atccttgatt   caaagataag   tatatgcctt   ctccttccgg   ctcttttcaa   tataccaaat  1620
```

FIG. 17A

```
aatatccatc  ctttgtttct  tttgttatat  tctcatcata  tattgaaatc  caaggaactt  1680
tactatagtt  ccagtagca   accttccta   caactgaata  tttatcttct  tttatatgca  1740
cttttaactg  cttgggtaac  ttatcatgga  ctaaagtttt  atatagatca  cctttatccc  1800
aatcagattt  tttaactaca  ttattggtac  gtttctcttt  aattaattta  aggacctgca  1860
taaagttgtc  tatcatttga  aattcccctcc tattataaaa  tatattatgt  ctcattttct  1920
tcaatatgta  ctatatttata ttttaccgta  atttactata  tttagttgca  gaaagaattt  1980
tctcaaagct  agaactttgc  ttcactataa  gtattcagta  taaagaatat  ttcgctatta  2040
tttacttgaa  atgaaagact  gcggaggcta  actatgtcaa  aaatcatgaa  cctcattact  2100
tatgataagc  ttcttaaaaa  cataacagca  attcacataa  acctcatatg  ttctgataca  2160
ttccaaatcc  ctttatgaag  cggctgaaaa  aaccgcatca  tttatgatat  gcttctccac  2220
gcataatctt  aaatgctcta  tacacttgct  caattaacac  aacccgcatc  atttgatgtg  2280
ggaatgtcat  tttgctgaat  gatagtgcgt  agttactgcg  ttgtaagacg  tccttgtgca  2340
ggccgtttga  tccgccaatg  acgaatacaa  agtcgctttg  cccttg                  2386
```

FIG. 17B

NUCLEOTIDE SEQUENCE OF NCTC10442J3rc

```
atattttacc  gtaatttact  atatttagtt  gcagaaagaa  ttttctccaa  gctagaactt   60
tgcttcacta  taagtattca  gtatagagaa  tatttcgcta  ttatttactt  gaaatgaaag  120
actgcggagg  ctaactatgt  caaaaatcat  gaacctcatt  acttatgata  agcttctcct  180
cgcataatct  taaatgctct  gtacacttgt  tcaattaaca  caacccgcat  catttgatgt  240
gggaatgtca  ttttgctgaa  tgatagtgcg  tagttactgc  gttgtaagac  gtccttgtgc  300
aggccgtttg  atccgccaat  gacgaaaaca  aagtcgcttt                          340
```

FIG. 18

NUCLEOTIDE SEQUENCE OF pSJ10-3J3rc

```
cagttattat   atattctaga   tcatcaatag   ttgaaaatg    gtttattaaa   cactctataa    60
acatcgtatg   atattgcaag   gtataatcca   atatttcata   tatgtaattc   ctccacatct   120
cattaaattt   ttaaattata   cacaacctaa   tttttagttt   tatttatgat   acgcttctcc   180
acgcataatc   ttaaatgctc   tgtacacttg   ttcaattaac   acaacccgca   tcatttgatg   240
tgggatgtc    atttgctga    atgatagtgc   gtagttactg   cgttgtaaga   cgtccttgtg   300
caggccgttt   gatccgccaa   tgacgaa                                             327
```

FIG. 19

SEQUENCE LISTING

<160> NUMBER OF SEQ ID NOS: 48

<210> SEQ ID NO 1
<211> LENGTH: 1809
<212> TYPE: DNA
<213> ORGANISM: Staphlococcus Aureus

<400> SEQUENCE: 1

```
gaattcgata gttttttag caataaagta tctaatactt ctattttatt caagtctttt      60
aaagttacta ttctaggaaa ttcactaatt ttttgaggaa gattaataat agcgtttatt     120
tctttgatta tcacactaat tttatctatg aattgctgct ttctattcgg tacacgcaat     180
gaaatacttg taccacaagt catcgttttt ccaaaaattt gaggattctg tggatgtcct     240
tggactgata tataagattc tgaaggtcta acgtaatcta cactattcct tctataatta     300
acaatctctt taagcctgtt ttgttgaaaa aaattaacat ttttattaac tatgtcttca     360
tttttgattg ctctttctgc aaaatcaatt ccgaagtcat aatcaatcaa attatttata     420
tcatgatatg cttgtccaaa aggtataata tatacattat tttgtaatgt agtatcttct     480
ttgagaaata atattgcatc aaaatgatga ccggattctg aaaataaatt gtcatcttct     540
tcagtatcta ggtatacatt ctttattaat aattgccaat ctaatagttt tttgtctttt     600
ttacgtatat aaactttact aattaatttt aattcatttg aatcactaac aagttcttta     660
tcattaagca gttcataatt gtcatcattt aaagattcta gattctctaa aaaatttgta     720
tttgtttcct gaaaattata aatagattta taaatattaa tcttcatatt acacccctta     780
attatatttt acatctattt ccattattac attttatgag tctcgcaaat tgtcagtttt     840
taaattatga taattatttt ccaaatagtt tattaaaaaa ctacatcttt cttgattgat     900
actctttcaa atcttaataa aattctttga ccttattatt tacattctca atttcttgga     960
attgttcttt tgaaacttca ttggtatatt tactattttt tgtcaatatc tgtaatttta    1020
tttatgatta tttatcatta cttagctacg tcaatgactg ttgattatga ataactgtt    1080
tctattgcaa agttactttt ataatttaat aaggacaaaa agaagcattc tatattaatc    1140
attttagata taaaccaatt tgatagggcc taatttcaac tgttagctac tacttaagtt    1200
atatgcgcaa ttatcgtgat atatcttata tattgaatga acgtggattt aatgtccacc    1260
atttaacacc ctccaaatta ttatctcctc atacagaatt ttttagtttt acttatgata    1320
cgcctctgcg tatcagttaa tgatgaggtt tttttaattg tcctttaatt tttcttcaat    1380
caaaggctcc actcctctat taattaaacc tttaattaag tcttgtgccg aaaatctatt    1440
tacagaccaa gcaacataat ttagcactct agctgctgtt tcattcactc tataactgaa    1500
gttattacat aaaatcatat atgctaattt agcaaaagga tcgtagtctt caaaccttcc    1560
acaaaactct tgatactttc tattaatact ctctattaaa tcacatgctg aagattcgtt    1620
tttttgcata taacgaatta aacacgcttg ctcattatta ttagaactta gaaccatttg    1680
acataattgt tcatcacttc gtgtcataat aaattcttcg ctttcatcat caaacactcc    1740
tcttttcagc ttttcttgac attttcgac gtgctttgca ctactgtgat actctaaaat    1800
tctctgcag                                                             1809
```

<210> SEQ ID NO 2
<211> LENGTH: 778
<212> TYPE: DNA
<213> ORGANISM: Staphlococcus Aureus -continued

```
<400> SEQUENCE: 2
atctgtaatt ttatttatga ttatttatca ttacttagct acgtcaatga ctgttgatta      60
tgaaataact gtttctattg caaagttact tttataattt aataaggaca aaagaagca      120 ttctatatta atcattttag atataaacca atttgatagg gcctaatttc aactgttagc     180
tactacttaa gttatatgcg caattatcgt gatatatctt atatattgaa tgaacgtgga     240
tttaatgtcc accatttaac accctccaaa ttattatctc ctcatacaga attttttagt     300
tttacttatg atacgcctct gcgtatcaga taatgatgcg gtttttaatt attgataagg     360
attgccatac ttattacaat actcatagaa gcctctttga tacatataga tttgcctttc     420
aatattttct ttactatcaa attcaagtcc ttttaaaatg agttcggcaa actctaatgc     480
tgccgttcca ttagcagtaa ctaaatttcg atctttttct gtaataattc aacaaattta     540
tgctttaaca actttaaaaa agacaatttc actattgagc tcttagatta taagttcagt     600
agcacaaatt gcaaatgctc tatctaattc tgtgactgtt taataaaac gttaacattt      660 atcctcactt aactctatca catcataatt cattaacaga ttgacgaact tatctgtgtc     720
tatgattgta ttgtgattta tccaagtttt tatattttta agcccttctt ccaagctt      778

<210> SEQ ID NO 3
<211> LENGTH: 564
<212> TYPE: DNA
<213> ORGANISM: Staphlococcus Aureus

<400> SEQUENCE: 3
gtcaacttat cagctaattc tttataatag ctaacccacg ttttatctat acacttcatc      60
acaatatccc ctccgttgta attacaatgt attatggaaa gatagaaaat actacttttc     120
aaaattatcc ccttgcaaat aaatttttct ataaatctat tagtttacta gattaataaa     180
tttcaatgtc gctaagtgca ttttattctt gttattattt aatttgaaaa acctgcttaa     240
ataatgataa tcacttacat aaacatcgta ctttatgata agtcacaagg taaaaaactc     300
ctccgctact tatgatacgc ttctgcttat cagttgatga tgcggttttt aagtaataag     360
ttcatcaaaa aaataattgg cttattatga acaactaaca gaattgattc caattatact     420
acttcacaat ttatatagta atcttcaata gatatgattt ttaattttaa attattaact     480
acaatcacct cataataatg gctttcttcg cctgttaaat tacctacata gaaagctggt     540
gttccttttt ttacttttac ccgt                                             564

<210> SEQ ID NO 4
<211> LENGTH: 2386
<212> TYPE: DNA
<213> ORGANISM: Staphlococcus Aureus

<400> SEQUENCE: 4
atctcttcaa tttatttta tatgaatcct gtgactcaat gattgtaata tctaaagatt       60
tcagttcatc atagacaatg ttcttttcaa cattttttat agcaaattga ttaaataaat     120
tctctaattt ctcccgtttg atttcactac catagattat attatcattg atatagtcaa     180
tgaataatga caaattatca ctcataacag tcccaacccc tttctttga tagactaatt      240 atcttcatca ttgtaaaaca aattacaccc tttaaattta actcaactta aatatcgaca     300
aattaaaaaa caataaaatt acttgaatat tattcataat atattaacaa ctttattata     360 ctgctctttta tatataaaat cattaataat taaacaagcc ttaaaatatt taactttttt    420
```

-continued

```
gtgattatta cacattatct tatctgctct ttatcaccat aaaaatagaa aaacaagat    480 tcctaaagaa tataggaatc ttgtttcaga ctgtggacaa actgattttt tatcagttag   540
cttatttaga aagttttatt taaattacag tttctatttt tattagatca caatttttatt  600 ttagctcttg ttcaagtaat cattttttcgc caaaaacttt atactgaata gcttctacat  660
taaatacttt gtcaatgaga tcatctacat cttttaaattc agaataattt gcatatggat  720
ctataaaata aaattgtggt tctttaccgg aaacattaaa tattcttaat attaaatatt   780
tctgcttata ttctttcata gcaaacattt catttagcga cataaaaaat ggttcctcaa   840
tactagaaga tgtagatgtt ttaatttcaa taaatttttc tacagcttta tctgtatttg   900
ttggatcaaa agctactaaa tcatagccat gaccgtgttg agagcctgga ttatcattta   960
aaatattcct aaactgttct ttcttatctt cgtctatttt attatcaatt agctcattaa  1020
agtaatttag cgctaatttt tctccaactt taccggttaa tttattctct ttatttgatt  1080
tttcaatttc tgaatcattt ttagtagtct ttgatacacc ttttttatat tttggaatta  1140
ttcctttagg tgcttccact tccttgagtg tcttatcttt ttgtgctgtt ctaatttctt  1200
caatttcgct gtcttcctgt atttcgtcta tgctattgac caagctatca taggatgttt  1260
ttgtaacttt tgaagctaat tcattaaata gttctaaaaa tttctttaaa tcctctagca  1320
tatcttcttc tgtgaatcct tcattcaaat cataatatttt gaatcttatt gatccatgag  1380
aatatcctga tggataatca tttttttaaat cataagatga atctttatttt tctgcgtaat  1440 aaaatcttcc agtattaaat tcatttgatg taatatattt attgagttcg gaagataaag  1500
ttaatgctct ttgttttgca gcattttttat cccgcggaaa catatcactt atctttgacc  1560
atccttgatt caaagataag tatatgcctt ctccttccgg atgaaaaaga tataccaaat  1620
aatatccatc ctttgtttct tttgttatat tctcatcata tattgaaatc caaggaactt  1680
tactatagtt cccagtagca accttcccta caactgaata tttatcttct tttatatgca  1740
cttttaactg cttgggtaac ttatcatgga ctaaagttttt atatagatca cctttatccc  1800
aatcagattt tttaactaca ttattggtac gtttctcttt aattaattta aggacctgca  1860
taaagttgtc tatcatttga aattccctcc tattataaaa tatattatgt ctcattttct  1920
tcaatatgta cttatttata ttttaccgta atttactata tttagttgca gaaagaatttt  1980 tctcaaagct agaactttgc ttcactataa gtattcagta taagaatat ttcgctatta   2040 tttacttgaa atgaaagact gcggaggcta actatgtcaa aaatcatgaa cctcattact  2100
tatgataagc ttcttaaaaa cataacagca attcacataa acctcatatg ttctgataca  2160
ttcaaaatcc ctttatgaag cggctgaaaa aaccgcatca tttatgatat gcttctccac  2220
gcataatctt aaatgctcta tacacttgct caattaacac aacccgcatc atttgatgtg  2280
ggaatgtcat tttgctgaat gatagtgcgt agttactgcg ttgtaagacg tccttgtgca  2340
ggccgtttga tccgccaatg acgaatacaa agtcgctttg cccttg                 2386
```

```
<210> SEQ ID NO 5
<211> LENGTH: 340
<212> TYPE: DNA
<213> ORGANISM: Staphlococcus Aureus

<400> SEQUENCE: 5
atattttacc gtaatttact atatttagtt gcagaaagaa ttttctccaa gctagaactt     60
tgcttcacta taagtattca gtatagagaa tatttcgcta ttatttactt gaaatgaaag   120
actgcggagg ctaactatgt caaaaatcat gaacctcatt acttatgata agcttctcct   180
```

```
cgcataatct taaatgctct gtacacttgt tcaattaaca caacccgcat catttgatgt      240
gggaatgtca ttttgctgaa tgatagtgcg tagttactgc gttgtaagac gtccttgtgc      300
aggccgtttg atccgccaat gacgaaaaca aagtcgcttt                           340

<210> SEQ ID NO 6
<211> LENGTH: 327
<212> TYPE: DNA
<213> ORGANISM: Staphlococcus Aureus

<400> SEQUENCE: 6
cagttattat atattctaga tcatcaatag ttgaaaaatg gtttattaaa cactctataa       60
acatcgtatg atattgcaag gtataatcca atatttcata tatgtaattc ctccacatct     120
cattaaattt ttaaattata cacaacctaa tttttagttt tatttatgat acgcttctcc     180
acgcataatc ttaaatgctc tgtacacttg ttcaattaac acaacccgca tcatttgatg     240
tggggatgtc attttgctga atgatagtgc gtagttactg cgttgtaaga cgtccttgtg     300
caggccgttt gatccgccaa tgacgaa                                         327

<210> SEQ ID NO 7
<211> LENGTH: 3183
<212> TYPE: DNA
<213> ORGANISM: Staphlococcus Aureus

<400> SEQUENCE: 7
ctgcagaggt aattattcca acaatacca ttgatttcaa aggagaaaga gatgacgtta       60
gaacgcgtga aacaaattta ggaaacgcga ttgcagatgc tatggaagcg tatggcgtta     120
agaatttctc taaaaagact gactttgccg tgacaaatgg tggaggtatt cgtgcctcta     180
tcgcaaaagg taaggtgaca cgctatgatt aatctcagt attaccattt ggaaatacga     240
ttgcgcaaat tgatgtaaaa ggttcagacg tctggacggc tttcgaacat agtttaggcg     300
caccaacaac acaaaaggac ggtaagacag tgttaacagc gaatggcggt ttactacata     360
tctctgattc aatccgtgtt tactatgata taaataaacc gtctggcaaa cgaattaatg     420
ctattcaaat tttaaataaa gagacaggta agtttgaaaa tattgattta aaacgtgtat     480
atcacgtaac gatgaatgac ttcacagcat caggtggcga cggatatagt atgttcggtg     540
gtcctagaga agaaggtatt tcattagatc aagtactagc aagttattta aaaacagcta     600
acttagctaa gtatgatacg acagaaccac aacgtatgtt attaggtaaa ccagcagtaa     660
gtgaacaacc agctaaagga caacaaggta gcaaaggtag taagtctggt aaagatacac     720
aaccaattgg tgacgacaaa gtgatggatc cagcgaaaaa accagctcca ggtaaagttg     780
ttttgttgct agcgcataga ggaactgtta gtagcggtac agaaggttct ggtcgcacaa     840
tagaaggagc tactgtatca agcaagagtg ggaaacaatt ggctagaatg tcagtgccta     900
aaggtagcgc gcatgagaaa cagttaccaa aactggaaac taatcaaagt tcaagcccag     960
aagcgatgtt tgtattatta gcaggtatag gtttaatcgc gactgtacga cgtagaaaag    1020
ctagctaaaa tatattgaaa ataatactac tgtatttctt aaataagagg tacggtagtg    1080 ttttttttatg aaaaaaagcg ataaccgttg ataaatatgg gatataaaaa cgaggataag    1140
taataagaca tcaaggtgtt tatccacaga aatggggata gttatccaga attgtgtaca    1200
atttaaagag aaatacccac aatgcccaca gagttatcca caaatacaca ggttatacac    1260
taaaaatcgg gcataaatgt caggaaaata tcaaaaactg caaaaaatat tggtataata    1320
```

```
agagggaaca gtgtgaacaa gttaataact tgtggataac tggaaagttg ataacaattt     1380
ggaggaccaa acgacatgaa aatcaccatt ttagctgtag ggaaactaaa agagaaatat     1440
tggaagcaag ccatagcaga atatgaaaaa cgtttaggcc catacaccaa gatagacatc     1500
atagaagttc cagacgaaaa agcaccagaa atatgagtg acaaagaaat tgagcaagta      1560
aaagaaaaag aaggccaacg aatactagcc aaaatcaaac cacaatccac agtcattaca    1620
ttagaaatac aaggaaagat gctatcttcc gaaggattgg cccaagaatt gaaccaacgc    1680
atgacccaag ggcaaagcga ctttgttttc gtcattggcg gatcaaacgg cctgcacaag    1740
gacgtcttac aacgcagtaa ctacgcacta tcattcagca aaatgacatt cccacatcaa    1800
atgatgcggg ttgtgttaat tgaacaagtg tacagagcat ttaagattat gcgaggagag    1860
gcgtatcata agtaaaacta aaaaattctg tatgaggaga taataaattg gagggtgtta    1920
aatggtggac attaaatcca cgttcattca atatataaga tatatcacga taattgcgca    1980
tataacttaa gtagtagcta acagttgaaa ttaggccta tcaaattggt ttatatctaa     2040
aatgattaat atagaatgct tctttttgtc cttattaaat tataaaagta actttgcaat    2100
agaaacagtt atttcataat caacagtcat tgacgtagct aagtaatgat aaataatcat    2160
aaataaaatt acagatattg acaaaaaata gtaaatattc caatgaagtt tcaaaagaac    2220
aattccaaga aattgagaat gtaaataata aggtcaaaga attttattaa gatttgaaag    2280
agtatcaatc aagaaagatg tagtttttta ataaactatt tggaaaataa ttatcataat    2340
ttaaaaactg acaatttgcg agactcataa aatgtaataa tggaaataga tgtaaaatat    2400
aattaagggg tgtaatatga agattaatat ttataaatct atttataatt ttcaggaaac    2460
aaatacaaat tttttagaga atctagaatc tttaaatgat gacaattatg aactgcttaa    2520
tgataaagaa cttgttagtg attcaaatga attaaaatta attagtaaag tttatatacg    2580
taaaaaagac aaaaaactat tagattggca attattaata agaatgtat acctagatac    2640 tgaagaagat gacaatttat tttcagaatc cggtcatcat tttgatgcaa tattatttct    2700
caaagaagat actacattac aaaataatgt atatattata ccttttggac aagcatatca    2760
tgatataaat aatttgattg attatgactt cggaattgat tttgcagaaa gagcaatcaa    2820
aaatgaagac atagttaata aaaatgttaa ttttttttcaa caaaacaggc ttaaagagat    2880
tgttaattat agaaggaata gtgtagatta cgttagacct tcagaatctt atatatcagt    2940
ccaaggacat ccacagaatc ctcaaatttt tggaaaaaca atgacttgtg gtacaagtat    3000
ttcattgcgt gtaccgaata gaaagcagca attcatagat aaaattagtg tgataatcaa    3060
agaaataaac gctattatta atcttcctca aaaaattagt gaatttccta gaatagtaac    3120
tttaaaagac ttgaataaaa tagaagtatt agatacttta ttgctaaaaa aactatcgaa    3180
ttc                                                                  3183
```

<210> SEQ ID NO 8
<211> LENGTH: 240
<212> TYPE: DNA
<213> ORGANISM: Staphlococcus Aureus

<400> SEQUENCE: 8

```
tatgttctga tacattccaa atcccttat gaagcggctg aaaaaaccgc atcatttatg      60
atatgcttct ccacgcataa tcttaaatgc tctatacact tgctcaatta acacaacccg    120
catcatttga tgtgggaatg tcatttttgct gaatgatagt gcgtagttac tgcgttgtaa    180
gacgtccttg tgcaggccgt ttgatccgcc aatgacgaat acaaagtcgc tttgcccttg    240
```

SEQ I NO 9

<211> LENGTH: 225
<212> TYPE: DNA
<213> ORGANISM: Staphlococcus Aureus

<400> SEQUENCE: 9

| ttcgtcattg gcggatcaaa cggcctgcac aaggacgtct tacaacgcag taactacgca | 60 |
| ctatcattca gcaaaatgac attcccacat caaatgatgc gggttgtgtt aattgaacaa | 120 |
| gtgtacagag catttaagat tatgcgtgga gaggcgtatc acaaataaaa ctaaaaatgg | 180 |
| agtaactatt aatatagtat aaattcaata tggtgataaa aacag | 225 |

<210> SEQ ID NO 10
<211> LENGTH: 225
<212> TYPE: DNA
<213> ORGANISM: Staphlococcus Aureus

<400> SEQUENCE: 10

| ttcgtcattg gcggatcaaa cggcctgcac aaggacgtct tacaacgcag taactacgca | 60 |
| ctatcattca gcaaaatgac attcccacat caaatgatgc gggttgtgtt aattgaacaa | 120 |
| gtgtacagag catttaagat tatgcgtgga gaggcgtatc acaaataaaa ctaaaaatgg | 180 |
| agtaactatt aatatagtat aaattcaata tggtgataaa aacag | 225 |

<210> SEQ ID NO 11
<211> LENGTH: 225
<212> TYPE: DNA
<213> ORGANISM: Staphlococcus Aureus

<400> SEQUENCE: 11

| ttcgtcattg gcggatcaaa cggcctgcac aaggacgtct tacaacgcag taactacgca | 60 |
| ctatcattca gcaaaatgac attcccacat caaatgatgc gggttgtgtt aattgaacaa | 120 |
| gtgtacagag catttaagat tatgcgagga gaggcgtatc ataagtaaaa ctaaaaaatt | 180 |
| ctgtatgagg agataataat ttggagggtg ttaaatggtg gacat | 225 |

<210> SEQ ID NO 12
<211> LENGTH: 225
<212> TYPE: DNA
<213> ORGANISM: Staphlococcus Aureus

<400> SEQUENCE: 12

| ttcgtcattg gcggatcaaa cggcctgcac aaggacgtct tacaacgtag taactacgca | 60 |
| ctatcattca gcaaaatgac atttccacat caaatgatgc gggttgtgtt aattgaacaa | 120 |
| gtgtacagag catttaagat tatgcgtgga gaggcgtatc ataagtaatg aggttcatga | 180 |
| tttttgacat agttagcctc cgcagtcttt caagtaaata atatc | 225 |

<210> SEQ ID NO 13
<211> LENGTH: 225
<212> TYPE: DNA
<213> ORGANISM: Staphlococcus Aureus

<400> SEQUENCE: 13

| ttcgtcattg gcggatcaaa cggcctgcac aaggacgtct tacaacgcag taactatgca | 60 |
| ctatcattta gcaaaatgac attcccacat caaatgatgc gggttgtgtt aattgaacaa | 120 |
| gtgtatagag catttaagat tatgcgtgga gaggcgtatc ataagtgatg cttgttagaa | 180 |

```
tgattttaa caatatgaaa tagctgtgga agctcaaaca tttgt              225

<210> SEQ ID NO 14
<211> LENGTH: 337
<212> TYPE: DNA
<213> ORGANISM: Staphlococcus Aureus

<400> SEQUENCE: 14
ctcattactt atgataagct tcttaaaaac ataacagcaa ttcacataaa cctcatatgt    60
tctgatacat tcaaaatccc tttatgaagc ggctgaaaaa accgcatcat ttatgatatg   120
cttctccacg cataatctta aatgctctat acacttgctc aattaacaca acccgcatca   180
tttgatgtgg gaatgtcatt ttgctgaatg atagtgcgta gttactgcgt tgtaagacgt   240
ccttgtgcag gccgtttgat ccgccaatga cgaatacaaa gtcgctttgc ccttgggtca   300
tgcgttggtt caattcttgg gccaatcctt cggaaga                            337

<210> SEQ ID NO 15
<211> LENGTH: 336
<212> TYPE: DNA
<213> ORGANISM: Staphlococcus Aureus

<400> SEQUENCE: 15
ctcattactt atgataagct tcttaaaaac ataacagcaa ttcacataaa cctcatatgt    60
tctgatacat tcaaaatccc tttatgaagc ggctgaaaaa accgcatcat ttatgatatg   120
cttcgcctct catgatctta aatgcgcgat aaatttgttc gatcaatatg acgcgcatat   180
ttggtgtggg aaggtcatat tgctaaaaga taaagcatag ttgctgcgtt gtaagacgtc   240
ttggtgtaaa ccattggagc cacctatgac aaatgtaaag tcgctttgac cttgtgtcat   300
gcgtgtttgt agttctttag cgagtccttc tgaaga                             336

<210> SEQ ID NO 16
<211> LENGTH: 260
<212> TYPE: DNA
<213> ORGANISM: Staphlococcus Aureus

<400> SEQUENCE: 16
ctcattactt atgataagct tcttaaaaac ataacagcaa tccacataaa cctcatatgt    60
tctgatacat tcaaaatccc tttatgaagc ggctgaaaaa accgcatcat ttatgatatg   120
cttccctcgc atgattttaa atgctctgta tacttgctcg attaagacaa cgcgcatcat   180
ttgatgtggg aatgtcattt tactgaatga aagtgcgtag ttgctgcgtt gtaagacgtc   240
ctcatgcaat ccatttgatc                                               260

<210> SEQ ID NO 17
<211> LENGTH: 262
<212> TYPE: DNA
<213> ORGANISM: Staphlococcus Aureus

<400> SEQUENCE: 17
ctcattactt atgataagct tcttaaaaac ataacagcaa ttcacataaa cctcatatgt    60
tctgatacat tcaaaatccc tttatgaagc ggctgaaaaa accgcatcat ttatgatatg   120
cttctcccta tcagtgattt tgctaaaaaa ttttaaagt tattatttt tcaacaaata    180 ctttagaggg ttttattatt aaatattaac tttatttaaa ttttaaagtc ttttaatat   240 tgataangat ctccctatag tg                                            262
```

```
<210> SEQ ID NO 18
<211> LENGTH: 21
<212> TYPE: DNA
<213> ORGANISM: Staphlococcus Aureus

<400> SEQUENCE: 18
gatagactaa ttatcttcat c                                             21

<210> SEQ ID NO 19
<211> LENGTH: 21
<212> TYPE: DNA
<213> ORGANISM: Staphlococcus Aureus

<400> SEQUENCE: 19
cagactgtgg acaaactgat t                                             21

<210> SEQ ID NO 20
<211> LENGTH: 20
<212> TYPE: DNA
<213> ORGANISM: Staphlococcus Aureus

<400> SEQUENCE: 20
tgagatcatc tacatcttta                                               20

<210> SEQ ID NO 21
<211> LENGTH: 20
<212> TYPE: DNA
<213> ORGANISM: Staphlococcus Aureus

<400> SEQUENCE: 21
ggatcaaaag ctactaaatc                                               20

<210> SEQ ID NO 22
<211> LENGTH: 20
<212> TYPE: DNA
<213> ORGANISM: Staphlococcus Aureus

<400> SEQUENCE: 22
atgctctttg ttttgcagca                                               20

<210> SEQ ID NO 23
<211> LENGTH: 23
<212> TYPE: DNA
<213> ORGANISM: Staphlococcus Aureus

<400> SEQUENCE: 23
atgaaagact gcggaggcta act                                           23

<210> SEQ ID NO 24
<211> LENGTH: 23
<212> TYPE: DNA
<213> ORGANISM: Staphlococcus Aureus

<400> SEQUENCE: 24
atattctaga tcatcaatag ttg                                           23

<210> SEQ ID NO 25
<211> LENGTH: 21
<212> TYPE: DNA
<213> ORGANISM: Staphlococcus Aureus

<400> SEQUENCE: 25
aagaattgaa ccaacgcatg a                                             21
```

```
<210> SEQ ID NO 26
<211> LENGTH: 21
<212> TYPE: DNA
<213> ORGANISM: Staphlococcus Aureus

<400> SEQUENCE: 26
aaacgacatg aaaatcacca t                                              21

<210> SEQ ID NO 27
<211> LENGTH: 23
<212> TYPE: DNA
<213> ORGANISM: Staphlococcus Aureus

<400> SEQUENCE: 27
tcgggcataa atgtcaggaa aat                                            23

<210> SEQ ID NO 28
<211> LENGTH: 21
<212> TYPE: DNA
<213> ORGANISM: Staphlococcus Aureus

<400> SEQUENCE: 28
gttcaagccc agaagcgatg t                                              21

<210> SEQ ID NO 29
<211> LENGTH: 33
<212> TYPE: DNA
<213> ORGANISM: Staphlococcus Aureus

<400> SEQUENCE: 29
ttattaggta aaccagcagt aagtgaacaa cca                                 33

<210> SEQ ID NO 30
<211> LENGTH: 18
<212> TYPE: DNA
<213> ORGANISM: Staphlococcus Aureus

<400> SEQUENCE: 30
gaaagaggcg gaggctaa                                                  18

<210> SEQ ID NO 31
<211> LENGTH: 18
<212> TYPE: DNA
<213> ORGANISM: Staphlococcus Aureus

<400> SEQUENCE: 31
catctaaaca tcgtatga                                                  18

<210> SEQ ID NO 32
<211> LENGTH: 20
<212> TYPE: DNA
<213> ORGANISM: Staphlococcus Aureus

<400> SEQUENCE: 32
aaacgggaac ccagtacgca                                                20

<210> SEQ ID NO 33
<211> LENGTH: 23
<212> TYPE: DNA
<213> ORGANISM: Staphlococcus Aureus

<400> SEQUENCE: 33
```

-continued gctgaatgat agtgcgtagt tac                                                23

<210> SEQ ID NO 34
<211> LENGTH: 18
<212> TYPE: DNA
<213> ORGANISM: Staphlococcus Aureus

<400> SEQUENCE: 34
tgaagacgtc cttgtgca                                                      18

<210> SEQ ID NO 35
<211> LENGTH: 25
<212> TYPE: DNA
<213> ORGANISM: Staphlococcus Aureus

<400> SEQUENCE: 35
tgaatgatag tgcgtagtta ctgcg                                              25

<210> SEQ ID NO 36
<211> LENGTH: 20
<212> TYPE: DNA
<213> ORGANISM: Staphlococcus Aureus

<400> SEQUENCE: 36
tcatttgatg tgggaatgtg                                                    20

<210> SEQ ID NO 37
<211> LENGTH: 22
<212> TYPE: DNA
<213> ORGANISM: Staphlococcus Aureus

<400> SEQUENCE: 37
gatcaaatgg attgcatgag ga                                                 22

<210> SEQ ID NO 38
<211> LENGTH: 20
<212> TYPE: DNA
<213> ORGANISM: Staphlococcus Aureus

<400> SEQUENCE: 38
tcttcagaag gactcgctaa                                                    20

<210> SEQ ID NO 39
<211> LENGTH: 1838
<212> TYPE: DNA
<213> ORGANISM: Staphlococcus Aureus

<400> SEQUENCE: 39
gaattcgata gttttttag caataaagta tctaatactt ctattttatt caagtctttt          60
aaagttacta ttctaggaaa ttcactaatt ttttgaggaa gattaataat agcgtttatt        120
tctttgatta tcacactaat tttatctatg aattgctgct ttctattcgg tacacgcaat        180
gaaatacttg taccacaagt cattgttttt ccaaaaattt gaggattctg tggatgtcct        240
tggactgata tataagattc tgaaggtcta acgtaatcta cactattcct tctataatta        300
acaatctctt taagcctgtt ttgttgaaaa aaattaacat ttttattaac tatgtcttca        360
tttttgattg ctctttctgc aaaatcaatt ccgaagtcat aatcaatcaa attatttata        420
tcatgatatg cttgtccaaa aggtataata tatacattat tttgtaatgt agtatcttct        480
ttgagaaata atattgcatc aaaatgatga ccggattctg aaaataaatt gtcatcttct        540
tcagtatcta ggtatacatt ctttattaat aattgccaat ctaatagttt tttgtcttt        600

-continued

```
ttacgtatat aaactttact aattaatttt aattcatttg aatcactaac aagttcttta      660
tcattaagca gttcataatt gtcatcattt aaagattcta gattctctaa aaaatttgta      720
tttgtttcct gaaaattata aatagattta taaatattaa tcttcatatt acacccctta      780
attatatttt acatctattt ccattattac attttatgag tctcgcaaat tgtcagtttt      840
taaattatga taattatttt ccaaatagtt tattaaaaaa ctacatcttt cttgattgat      900
actctttcaa atcttaataa aattctttga ccttattatt tacattctca atttcttgga      960
attgttcttt tgaaacttca ttggaatatt tactatttt tgtcaatatc tgtaatttta     1020
tttatgatta tttatcatta cttagctacg tcaatgactg ttgattatga ataactgtt     1080 tctattgcaa agttactttt ataatttaat aaggacaaaa agaagcattc tatattaatc     1140
attttagata taaaccaatt tgataggcc taatttcaac tgttagctac tacttaagtt     1200
atatgcgcaa ttatcgtgat atatcttata tattgaatga acgtggattt aatgtccacc     1260
atttaacacc ctccaaatta ttatctcctc atacagaatt ttttagttttt acttatgata     1320 cgcctctcct cgcataatct aaatgctct gtacacttgt tcaattaaca caacccgcat     1380
catttgatgt gggaatgtca ttttgctgaa tgatagtgcg tagttactgc gttgtaagac     1440
gtccttgtgc aggccgtttg atccgccaat gacgaaaaca aagtcgcttt gcccttgggt     1500
catgcgttgg ttcaattctt gggccaatcc ttcggaagat agcatctttc cttgtatttc     1560
taatgtaatg actgtggatt gtggtttgat tttggctagt attcgttggc cttctttttc     1620
ttttacttgc tcaatttctt tgtcactcat attttctggt gcttttttcgt ctggaacttc     1680 tatgatgtct atcttggtgt atgggcctaa acgtttttca tattctgcta tggcttgctt     1740
ccaatatttc tcttttagtt tccctacagc taaaatggtg attttcatgt cgtttggtcc     1800
tccaaattgt tatcaacttt ccagttatcc acaagtta                             1838
```

<210> SEQ ID NO 40
<211> LENGTH: 300
<212> TYPE: DNA
<213> ORGANISM: Staphlococcus Aureus

<400> SEQUENCE: 40

```
atatgcgcaa ttatcgtgat atatcttata tattgaatga acgtggattt aatgtccacc       60
atttaacacc ctccaaatta ttatctcctc atacagaatt ttttagttttt acttatgata      120 cgcctctcct cgcataatct aaatgctct gtacacttgt tcaattaaca caacccgcat      180
catttgatgt gggaatgtca ttttgctgaa tgatagtgcg tagttactgc gttgtaagac      240
gtccttgtgc aggccgtttg atccgccaat gacgaaaaca aagtcgcttt gcccttgggt      300
```

<210> SEQ ID NO 41
<211> LENGTH: 823
<212> TYPE: DNA
<213> ORGANISM: Staphlococcus Aureus

<400> SEQUENCE: 41

```
attgttcttt tgaaacttca ttggtatatt tactattttt tgtcaatatc tgtaatttta       60
tttatgatta tttatcatta cttagctacg tcaatgactg ttgattatga ataactgtt      120 tctattgcaa agttactttt ataatttaat aaggacaaaa agaagcattc tatattaatc      180
attttagata taaaccaatt tgataggcc taatttcaac tgttagctac tacttaagtt      240
atatgcgcaa ttatcgtgat atatcttata tattgaatga acgtggattt aatgtccacc      300
```

```
atttaacacc ctccaaatta ttatctcctc atacagaatt ttttagtttt acttatgata        360
cgcctctgcg tatcagttaa tgatgaggtt tttttaattg tcctttaatt tttcttcaat        420
caaaggctcc actcctctat taattaaacc tttaattaag tcttgtgccg aaaatctatt        480
tacagaccaa gcaacataat ttagcactct agctgctgtt tcattcactc tataactgaa        540
gttattacat aaaatcatat atgctaattt agcaaaagga tcgtagtctt caaaccttcc        600
acaaaactct tgatactttc tattaatact ctctattaaa tcacatgctg aagattcgtt        660
tttttgcata taacgaatta aacacgcttg ctcattatta ttagaactta gaaccatttg        720
acataattgt tcatcacttc gtgtcataat aaattcttcg ctttcatcat caaacactcc        780
tcttttcagc ttttcttgac attttttcgac gtgctttgca cta                        823

<210> SEQ ID NO 42
<211> LENGTH: 240
<212> TYPE: DNA
<213> ORGANISM: Staphlococcus Aureus

<400> SEQUENCE: 42
tatgttctga tacattccaa atcccttat gaagcggctg aaaaaaccgc atcatttatg         60
atatgcttct ccacgcataa tcttaaatgc tctatacact tgctcaatta acacaacccg       120
catcatttga tgtgggaatg tcattttgct gaatgatagt gcgtagttac tgcgttgtaa       180
gacgtccttg tgcaggccgt ttgatccgcc aatgacgaat acaaagtcgc tttgcccttg       240

<210> SEQ ID NO 43
<211> LENGTH: 280
<212> TYPE: DNA
<213> ORGANISM: Staphlococcus Aureus

<400> SEQUENCE: 43
tgcttcacta taagtattca gtatagagaa tatttcgcta ttatttactt gaaatgaaag        60
actgcggagg ctaactatgt caaaaatcat gaacctcatt acttatgata agcttctcct       120
cgcataatct taaatgctct gtacacttgt tcaattaaca caacccgcat catttgatgt       180
gggaatgtca ttttgctgaa tgatagtgcg tagttactgc gttgtaagac gtccttgtgc       240
aggccgtttg atccgccaat gacgaaaaca aagtcgcttt                            280

<210> SEQ ID NO 44
<211> LENGTH: 240
<212> TYPE: DNA
<213> ORGANISM: Staphlococcus Aureus

<400> SEQUENCE: 44
tcaatatgta cttatttata ttttaccgta atttactata tttagttgca gaaagaattt        60
tctcaaagct agaactttgc ttcactataa gtattcagta taagaatat ttcgctatta       120 tttacttgaa atgaaagact gcggaggcta actatgtcaa aaatcatgaa cctcattact       180
tatgataagc ttcttaaaaa cataacagca attcacataa acctcatatg ttctgataca       240

<210> SEQ ID NO 45
<211> LENGTH: 176
<212> TYPE: DNA
<213> ORGANISM: Staphlococcus Aureus

<400> SEQUENCE: 45 atatttttacc gtaatttact atatttagtt gcagaaagaa ttttctccaa gctagaactt        60
tgcttcacta taagtattca gtatagagaa tatttcgcta ttatttactt gaaatgaaag       120
```

```
actgcggagg ctaactatgt caaaaatcat gaacctcatt acttatgata agcttc        176

<210> SEQ ID NO 46
<211> LENGTH: 240
<212> TYPE: DNA
<213> ORGANISM: Staphlococcus Aureus

<400> SEQUENCE: 46
tatgttctga tacattccaa atccctttat gaagcggctg aaaaaaccgc atcatttatg     60
atatgcttct ccacgcataa tcttaaatgc tctatacact tgctcaatta acacaacccg    120
catcatttga tgtgggaatg tcattttgct gaatgatagt gcgtagttac tgcgttgtaa    180
gacgtccttg tgcaggccgt ttgatccgcc aatgacgaat acaaagtcgc tttgcccttg    240

<210> SEQ ID NO 47
<211> LENGTH: 267
<212> TYPE: DNA
<213> ORGANISM: Staphlococcus Aureus

<400> SEQUENCE: 47
acatcgtatg atattgcaag gtataatcca atatttcata tatgtaattc ctccacatct     60
cattaaattt ttaaattata cacaacctaa tttttagttt tatttatgat acgcttctcc    120
acgcataatc ttaaatgctc tgtacacttg ttcaattaac acaacccgca tcatttgatg    180
tggggatgtc attttgctga atgatagtgc gtagttactg cgttgtaaga cgtccttgtg    240
caggccgttt gatccgccaa tgacgaa                                        267

<210> SEQ ID NO 48
<211> LENGTH: 642
<212> TYPE: DNA
<213> ORGANISM: Staphlococcus Aureus

<400> SEQUENCE: 48
attgttcttt tgaaacttca ttggtatatt tactattttt tgtcaatatc tgtaatttta     60
tttatgatta tttatcatta cttagctacg tcaatgactg ttgattatga aataactgtt    120
tctattgcaa agttactttt ataatttaat aaggacaaaa agaagcattc tatattaatc    180
attttagata taaaccaatt tgatagggcc taatttcaac tgttagctac tacttaagtt    240
atatgcgcaa ttatcgtgat atatcttata tattgaatga acgtggattt aatgtccacc    300
atttaacacc ctccaaatta ttatctcctc atacagaatt ttttagtttt acttatgata    360
cgcctctgcg tatcagttaa tgatgaggtt tttttaattg tcctttaatt tttcttcaat    420
caaaggctcc actcctctat taattaaacc tttaattaag tcttgtgccg aaaatctatt    480
tacagaccaa gcaacataat ttagcactct agctgctgtt tcattcactc tataactgaa    540
gttattacat aaaatcatat atgctaattt agcaaaagga tcgtagtctt caaaccttcc    600
acaaaactct tgatactttc tattaatact ctctattaaa tc                       642
```

METHOD OF IDENTIFYING METHICILLIN-RESISTANT *STAPHYLOCOCCUS AUREUS* OR METHICILLIN-RESISTANT COAGULASE-NEGATIVE STAPHYLOCOCCI

TECHNICAL FIELD

This invention relates to a diagnostic method for performing a genetic diagnosis of a resistant bacterium, especially for specifically detecting at high sensitivity methicillin-resistant *Staphylococcus aureus* (hereinafter referred to as "MRSA") and methicillin-resistant coagulase-negative staphylococci (hereinafter referred to as "MRC-NS"). Namely the present invention is concerned with a diagnostic method which can promptly detect and identify MRSA and MRC-NS.

BACKGROUND ART

MRSA and MRC-NS, including *Staphylococcus haemolyticus* and *Staphylococcus epidermidis*, are principal pathogenic bacteria of nosocomial infection at hospitals in all the countries of the world, and have become a serious clinical problem due to the limited availability of effective antibiotics. In clinical activities, their accurate and speedy identification has become an important theme for the diagnosis and treatment of infected patients.

MRSA is *Staphylococcus aureus* which produces PBP (penicillin-binding protein)2' (or PBP2a), that is, a cell-wall synthesizing enzyme PBP having low affinity to all β-lactam antibiotics developed to date led by methicillin. Because of the production of this PBP2', MRSA exhibits resistance to all the conventional β-lactam antibiotics. Since the report of its first clinical strain in England in 1961, it has spread around the whole world and at present, it has become, as a nosocomial infectious bacterium, a serious problem for the present-day medical treatments at hospitals in all the countries of the world.

MRSA produces PBP2' in addition to four PBPs which *Staphylococcus aureus* inherently have. In 1986, the mecA gene encoding this PBP was cloned by Matsuhashi et al. and its entire base sequence was determined by them. The mecA gene exists on chromosomes of MRSA and MRC-NS, but is not found on methicillin-susceptible *Staphylococcus aureus* (MSSA). Accordingly, the mecA gene is considered to be a gene adventitiously acquired on the chromosomes of *Staphylococcus aureus*. Detection of this mecA gene on the chromosomal DNA of *Staphylococcus aureus*, generally by PCR (polymerase chain reaction) or hybridization, makes it possible to identify it as MRSA or MRC-NS.

In Japan, a mecA identification kit by ED-PCR (enzyme detection PCR) was developed, and subsequent to its approval and the setting of its health insurance price by the Ministry of Health and Welfare, is now frequently used for clinical diagnoses (Ubukata, K., et al. *J. Clin. Microbiol.* 30, 1728–1733, 1992). However, the identification of MRSA by this method involves at least the following two problems.

1) It can be used only after a bacterium from a patient's sample has been cultured and procedures have then been conducted beforehand for the strain identification of *Staphylococcus aureus*. The above method therefore has a drawback of lack of promptness and creates various problems. Namely, the mecA gene is also distributed widely in other strains of the genus of *Staphylococcus* (S.) *epidermidis, S. haemolyticus, S. saprophyticus, S. capitis, S. warneri, S. sciuri* and *S. caprae* (Eiko Suzuki et al. *Antimicrb. Agents Chemother.* 37, 1219–1226, 1993). In a patient's sample, these mecA-containing Staphylococcus strains are detected at the same time in many instances. Accordingly, direct detection of the mecA gene from a sample cannot be taken as a proof of the existence of MRSA. This has led to a limitation of the detection method of the mecA gene having to be used after a strain has been cultured from a patient's sample and has then been confirmed to be *Staphylococcus aureus* by a conventional strain identification method. Accordingly, there has been no choice other than to rely upon an empiric therapy until an infected strain is identified. Further, administration of vancomycin has been indispensable even if the administration is eventually found to have been unnecessary.

2) Lack of internal control in PCR. Described specifically, false positive or false negative may be determined in PCR operations of nowadays, depending on the working conditions of a thermal cycler. Upon a judgment of positive or negative, it is desirable to have internal controls for negative and positive in each operation. This is however rarely performed in present-day diagnostic methods.

DISCLOSURE OF THE INVENTION

With a view to establishing a fast, simple and reliable, specific identification method of MRSA and MRC-NS, the present inventors have analyzed the genes of MRSA, MSSA and MRC-NS in more detail. The present inventors were interested in reports that an additional DNA of several tens of kilobases (kb) or greater exists in a methicillin-resistant locus (Beck, W. D. et al. *J. Bacteriol.* 165, 373–378, 1986; Skinner, S. et al. *Mol. Microbiol.* 2, 289–298, 1988).

The present inventors have then proceeded with extensive research to determine if any gene sequence specific to MRSA exists on chromosomes of MRSA and MRC-NS. The research has led to the finding and identification of a specific target DNA fragment, resulting in the completion of the present invention.

Namely, the present invention provides a diagnostic method of an MRSA (methicillin-resistant *Staphylococcus aureus*) or MRC-NS (methicillin-resistant coagulase-negative staphylococci), which comprises performing a reaction with a sample by making combined use of a part of a mecDNA, which is an integrated adventitious DNS existing on a chromosome of said MRSA or MRC-NS and carrying a mecA gene thereon, and a part of a nucleotide sequence of a chromosomal DNA surrounding said integrated DNA; and also a diagnostic method of an MRSA or MRC-NS by PCR, LCR, hybridization, PT-PCR or NASBA, which comprises performing a reaction with a sample by using a nucleotide sequence of a chromosomal DNA surrounding an integration site of a mecDNA in a chromosome of a methicillin-susceptible *Staphylococcus aureus* or methicillin-susceptible C-NS (MSC-NS), wherein said method makes use of an occurrence of a negative reaction when said sample contains a mecDNA integrated therein.

BRIEF DESCRIPTION OF THE DRAWINGS

FIG. 4 (consisting of FIG. 4A and FIG. 4B) is a diagram showing a restriction mapping of LD8325, including a mec integration site, and a partial nucleotide sequence thereof (SEQ ID NO:7). A vertical arrow indicates the mec integration site. A horizontal arrow indicates an orientation of the nucleotide sequence (from 5' toward 3'). An underlined part in the nucleotide sequence means an open reading frame of an intM. An arrowhead between the nucleotide numbers 1856 and 1857 indicates the mec integration site.

FIG. 5 (consisting of FIG. 5A and FIG. 5B) is a diagram showing nucleotide sequences of chromosomal DNAs flanking a mec integration site as compared among MSSA strains. Coagulase types produced by the respective strains: ATCC25923, type 4 (SEQ ID NO:9); STP23, type 4 (SEQ ID NO:10); NCTC8325, type 3 (SEQ ID NO:11); STP43, type 7 (SEQ ID NO:12); STP53, type 5 (SEQ ID NO13). Coagulase types produced by the respective strains: ATCC25923, type 4; STP23, Type 4; NCTC8325, type 3; STP43, type 7; STP53, type 5. Compared with 225 nucleotides of NCTC8325pLEC12, ranging from the nucleotide numbers 1708 to 1932, were the corresponding 225 nucleotides of the other strains. Boxed nucleotide are common to all the strains.

FIG. 6 (consisting of FIG. 6A and FIG. 6B) is a diagram showing a comparison in nucleotide sequence between MRSA and methicillin-resistant bacteria (the sequence of N315 is listed as SEQ ID NO:14). SH 518 (SEQ ID NO:16) and SH JA 178 (SEQ ID NO:17) are clinical strains of *S. haemolyticus*. SE G3 (SEQ ID NO:15) is a clinical strain of *S. epidermidis*.

FIG. 9 (consisting of FIG. 9A and FIG. 9B) and FIG. 10 (consisting of FIG. 10A and FIG. 10B) are diagrams showing homology between nucleotide sequences pLEC12rc (SEQ ID NO:39) and pSJ8-2a (SEQ ID NO:1). In FIG. 9, a. A nucleotide sequence of a subclone pSJ8-2a of N315, including an upstream junction of a mec region, (see FIG. 1) (the lower nucleotide sequence) and of a chromosomal intM, (the upper nucleotide sequence) were compared. The outer nucleotide sequences from the upstream junctions of the mec regions are substantially the same. pLEC12rc is reverse complementary in nucleotide sequence to pLEC12.

FIG. 10 is a diagram showing homology in nucleotide sequence between pLEC12rc and pSJ8-2a. Parts continued from FIG. 9 are shown (SEQ ID NO:1).

FIG. 11 is a diagram showing homology in nucleotide sequence between pLEC12rc (SEQ ID NO:40) and N315J3rc (SEQ ID NO:8). The nucleotide sequence of a subclone N315J3 of N315, including a downstream junction of the mec region, (see FIG. 1) (the lower nucleotide sequence) and the nucleotide sequence of a chromosomal DNA clone pLEC12(pLEC1a) of NCTC8325, including an intM, (the upper nucleotide sequence) are compared. The nucleotide sequences of the intM on outer sides of the mec region DNA are substantially the same. The nucleotide sequence of N315J3rc is reverse complementary to the nucleotide sequence of N315J3.

FIG. 12 (consisting of FIG. 12A and FIG. 12B) is a diagram comparing the nucleotide sequence of a clone including an upstream junction of a mec region of N315 with one of NCTC10442 (N315, the upper nucleotide sequence (SEQ ID NO:41); NCTC10442, the lower nucleotide sequence (SEQ ID NO:2). The nucleotide sequences of their mec regions are extremely different from each other except for IRs near the junctions. On the other hand, the nucleotide sequences on outer sides of the junctions are the same.

FIG. 13 is a diagram comparing the nucleotide sequence of a clone including a downstream junction of the mec region of N315 with one of NCTC10442, (N315, the upper nucleotide sequence (SEQ ID NO:42); NCTC10442, the lower nucleotide sequence (SEQ ID NO:43). The nucleotide sequences of their mec regions are extremely different from each other except for IRs. On the other hand, the nucleotide sequences on outer (downstream) sides of the junctions have extremely high homology. The nucleotide sequence of NCTC10442J3 is reverse complementary to the nucleotide sequence of NCTC10442J3.

FIG. 14 is a diagram comparing N315IS-J3rc with J3rc of NCTC10442. The upper nucleotide sequence (SEQ ID NO:44) corresponds to N315IS-J3 (see FIG. 1 and FIG. 17), while the lower nucleotide sequence (SEQ ID NO:45) is a sequence of first 176 nucleotides corresponding to a mec region of J3rc of NCTC10442 (see FIG. 13).

FIG. 15 is a diagram comparing N315J3rc with pSJ10-3J3rc. The upper nucleotide sequence (SEQ ID NO:46) corresponds to N315J3rc, while the lower nucleotide (SEQ ID NO:47) sequence corresponds to pSJ10-3J3rc. The nucleotide sequence of pSJ10-3J3rc is reverse complementary to the nucleotide sequence of pSJ10-3J3.

FIG. 16 (consisting of FIG. 16A and FIG. 16B) is a diagram comparing pSJ8-2a with LG12H2 (SEQ ID NO:3). The upper nucleotide sequence (SEQ ID NO:48) corresponds to pSJ8-2a, while the lower nucleotide sequence corresponds to LG12H2.

FIG. 17 (consisting of FIG. 17A and FIG. 17B) is a diagram showing a nucleotide sequence of N315IS-J3 (SEQ ID NO:4). A thin underline indicates a sequence of first 176 nucleotides corresponding to the mec region of J3rc of NCTC10442 (see FIG. 14). A thick underline designates a nucleotide sequence corresponding to an intM on an outer side of a downstream junction of a mec region.

FIG. 18 is a diagram showing a nucleotide sequence of NCTC10442J3rc (SEQ ID NO:5). An underline indicates a nucleotide sequence corresponding to an intM on an outer side of a downstream junction of a mec region.

FIG. 19 is a diagram showing a nucleotide sequence of pSJ10-3J3rc (SEQ ID NO:6). An underline indicates a nucleotide sequence corresponding to an intM on an outer side of a downstream junction of a mec region.

BEST MODE FOR CARRYING OUT THE INVENTION

Figure 1:
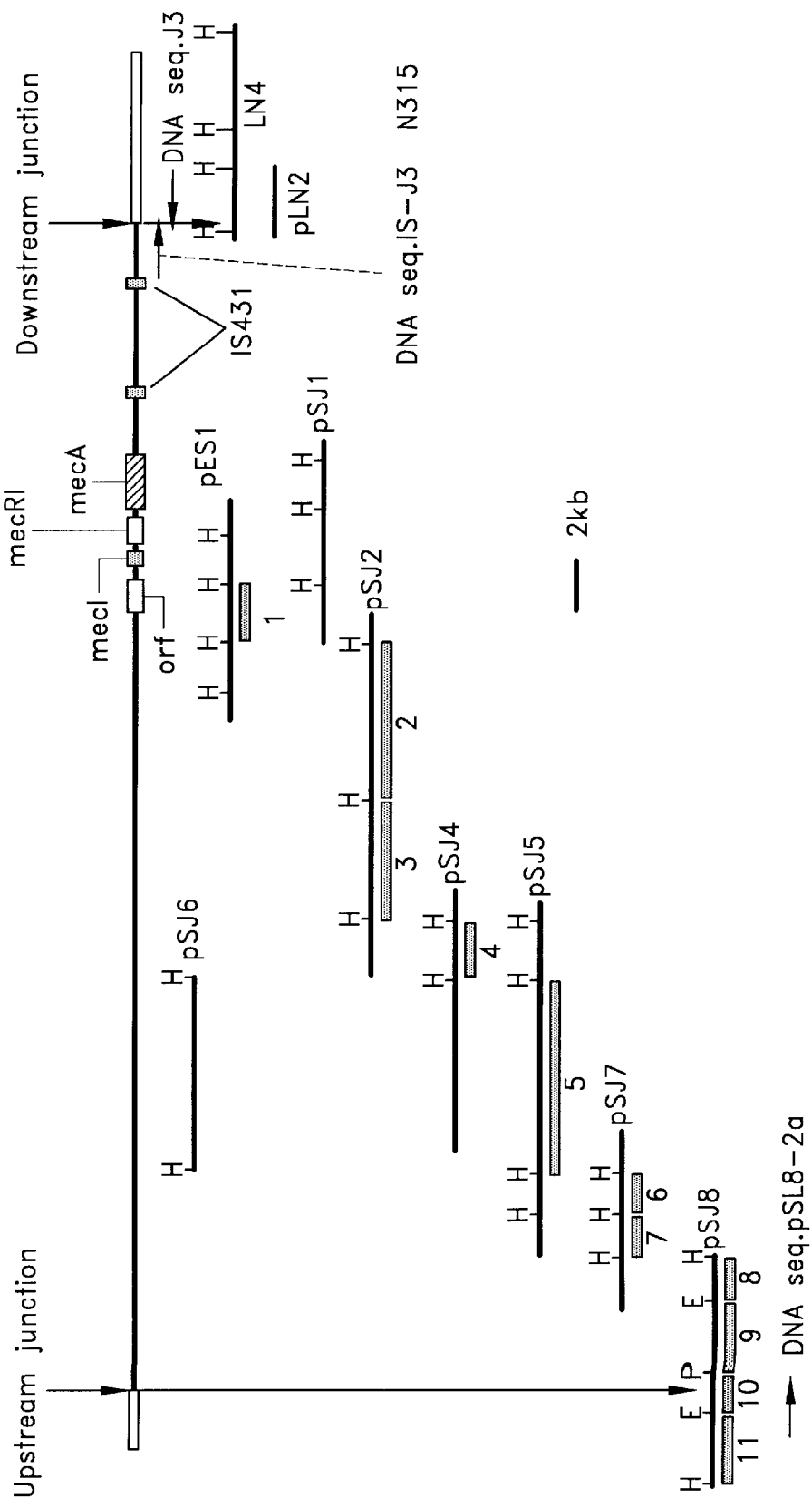
FIG. 1 is a diagram illustrating cloning of a mec region DNA of N315 by chromosome walking. H, P and E represent restriction sites by HindIII, PstI and EcoR1, respectively.
Figure 2:
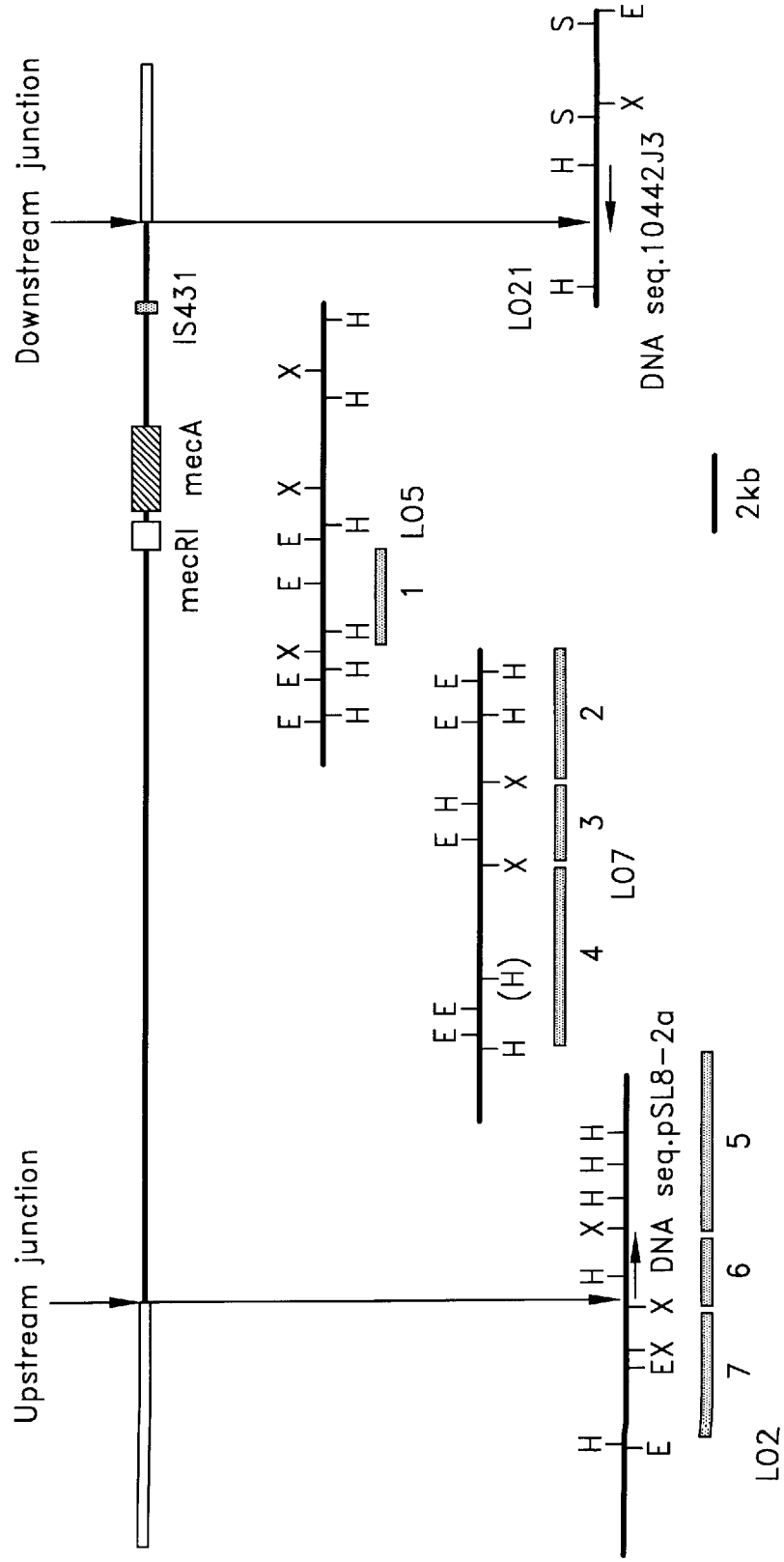
FIG. 2 is a diagram illustrating cloning of a mec region DNA of NCTC10442 by chromosome walking. The diagram shows restriction maps of clones L02, L05, L07 and L021 obtained from a λ phage library and an integration site of the mec region DNA. 1 to 7 indicate probes for the mec region DNA. Restriction sites: H, HindIII; E, EcoRI; S, SalI; X, XbaI.
Figure 3:
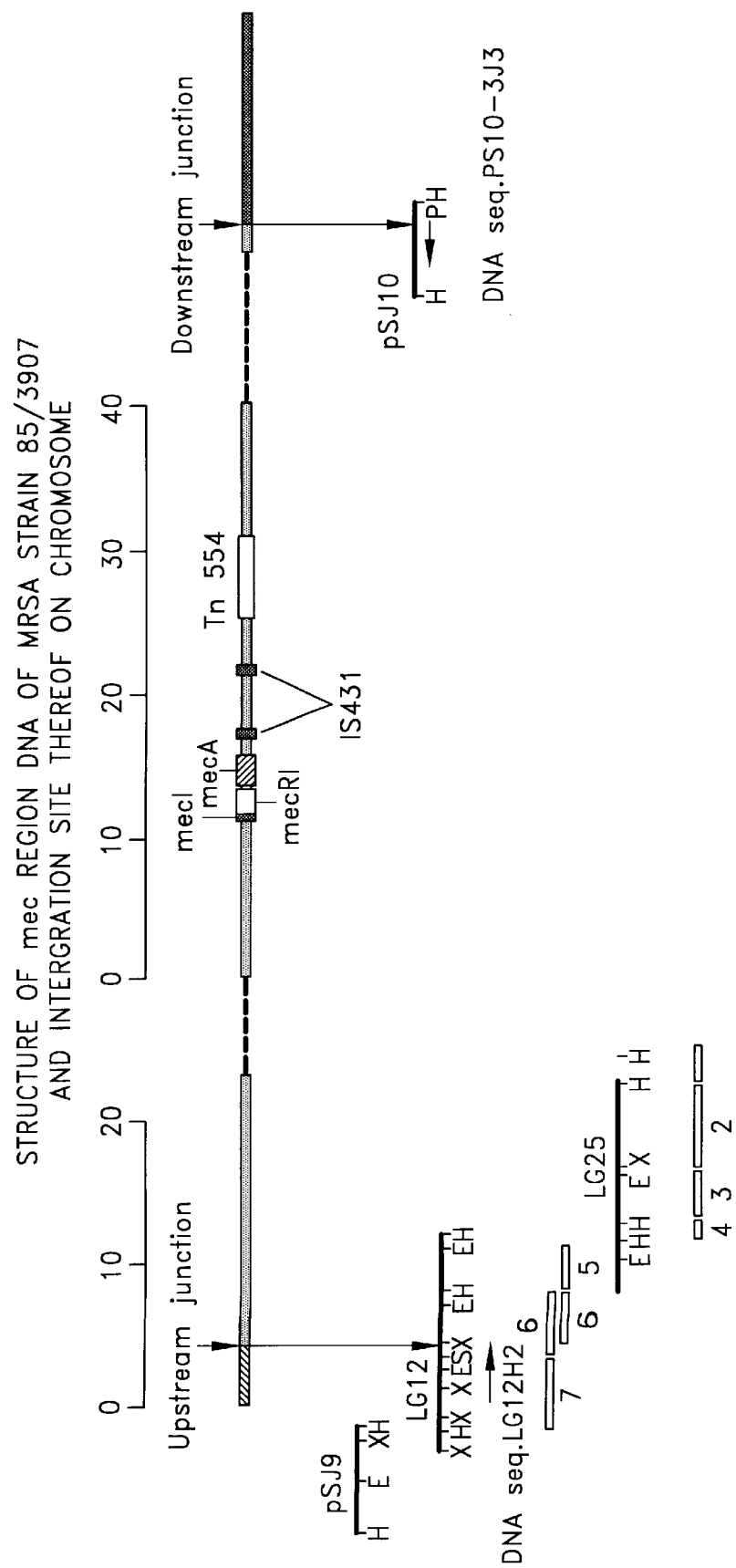
FIG. 3 is a diagram showing a structure of a mec region DNA of an MRSA strain 85/3907 and an integration site on its chromosome. Also shown are restriction maps of clones pSJ9 and pSJ10 obtained from a plasmid library and clones LG12 and LG25 obtained from a λ phage library as well as an integration site of the mec region DNA. 1 to 7 indicate probes for the mec region DNA. Restriction sites: H, HindIII; E, EcoRI; S, SalI; X, XbaI; P, PstI.

The present inventors determined the nucleotide sequences of the above DNA fragments, namely, the mec region DNAs [may hereinafter be referred to as "mec"; Keiichi Hiramatsu: *Microbiol. Immunol.* 38(8), 531–543, 1995] by chromosome walking subsequent to their cloning from MRSA N315 isolated in Japan (type-2 coagulase producing strain; type 2j MRSA), MRSA NCTC10442 isolated in U.K. (type-3 coagulase producing strain; type 3e MRSA) and MRSA 85/3907 isolated in Germany (type-4 coagulase producing strain; type 4e MRSA). These three strains are those chosen, as representative examples of epidemic strains isolated in various countries of the world, on the basis of classification according to ribotyping, the coagulase method and sites and natures of mutations by the determination of nucleotide sequences of mecI genes. As a result, as is shown in FIGS. 1, 2 and 3:

1) The mec DNAs have been found to be giant DNA regions of 52 Kb in N315, 33 Kb in NCTC10442 and 54 Kb or greater in 85/3907, and to be all composed of DNAs which do not undergo cross hybridization with chromosomal DNAs of many MSSAs studied as controls.

2) Each mec contains at opposite ends thereof inverted sequences (inverted repeats; hereinafter called "IR"s) of 20–30 bases (base pairs; bp).

Figure 4B:
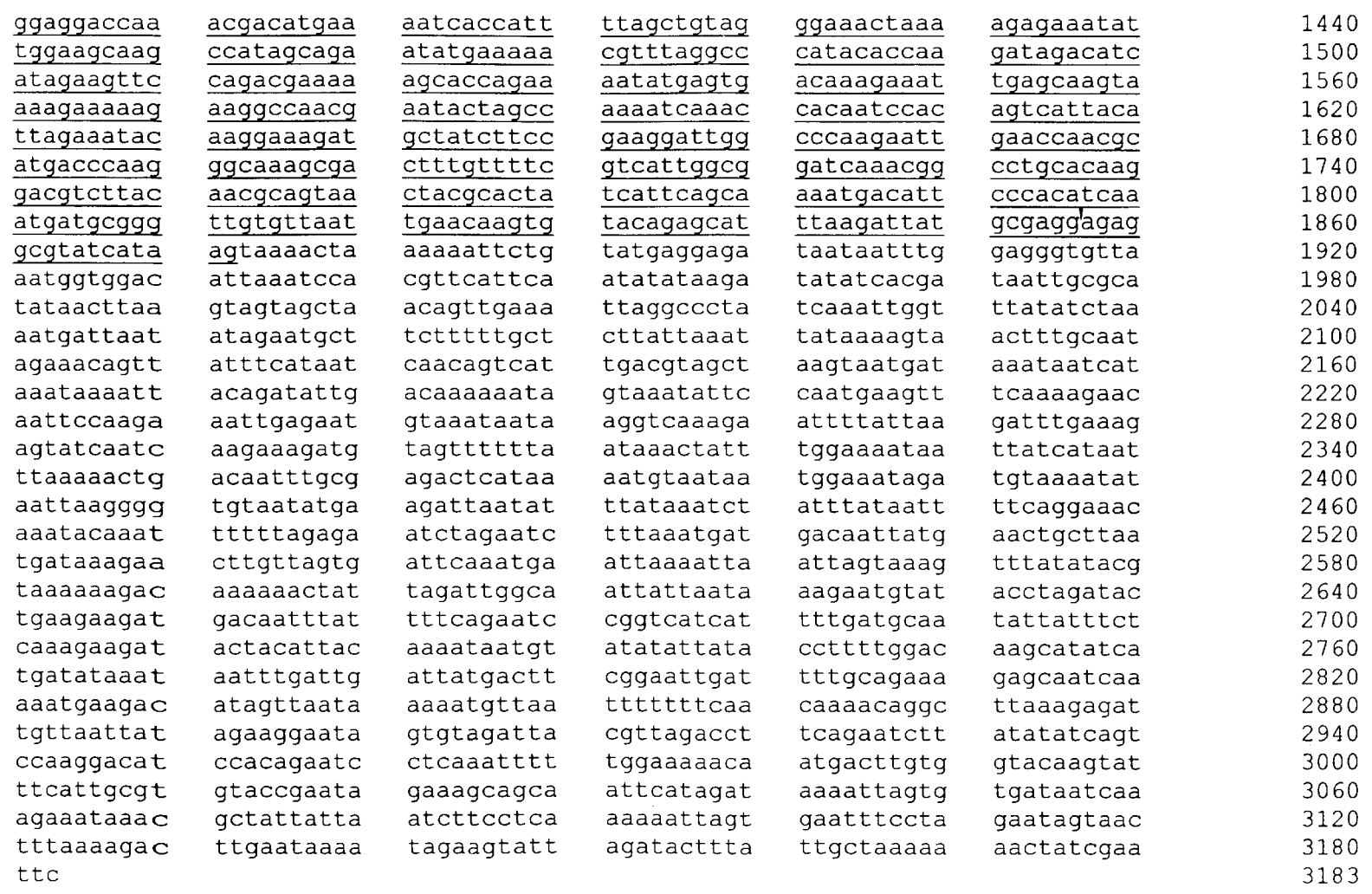

3) These mec regions DNAs have been found to be integrated in particular of (open reading frames) (hereinafter called "intM"s) on chromosomal DNAs of the *Staphylococcus aureus* strains (FIG. 4);

4) From a comparison among the nucleotide sequences of these three strains, it has been found that they are substantially different from each other on upstream sides of the mec region DNAs and that on downstream sides of the mec DNAs, N315 and NCTC10442 have the same nucleotide sequence whereas 85/3907 have a sequence different from the other two strains.

5) In each strain, the nucleotide sequence of the chromosomal DNA was well retained in a 5'-side region of the intM relative to the mec integration site and also in a region upstream from the intM (the left side in FIG. 4), and the nucleotide sequence of the chromosomal DNA in a 3'-side region of the intM relative to the mec integration site and also in a region downstream from the intM (the lower side in FIG. 4) was in 85/3907 (FIG. 16).

From the above facts, an intM gene was estimated to be an integration site for a mec region DNA. Accordingly, intM-containing DNA fragments of five MSSA strains of different origins were cloned, and their nucleotide sequences were determined (FIG. 5). As a result, 6) The intM genes all retained the same nucleotide sequences on 5'-sides relative to the mec integration sites, but their 3'-side nucleotide sequences were different.

7) Concerning the nucleotide sequences outside the intMs, the 5'-side nucleotide sequences upstream from the intMs were all retained but the 3'-side nucleotide sequences downstream from the intMs were different from one strain to another, whereby versatility was observed.

Next, to determine mec integration sites in Staphylococcus strains other than *Staphylococcus aureus*, DNA fragments containing downstream junctions of mec DNAs were cloned from *S. haemolyticus* clinocal strains JA178 and 495 and *S. epidermidis* clinical strain G3, all of which contained mecA genes, by using probes for downstream ends of the mec DNAs. Upon determination of their nucleotide sequences, 8) The nucleotide sequences of all the downstream ends of the mec DNAs were homologous with that of the mec of N315, but the nucleotide sequences on right extremity to mecDNA were considerably different from that of the intM in N315 (FIG. 6).

With a view to confirming that a chromosomal DNA of a Staphylococcus strain other than *Staphylococcus aureus* does not contain any gene having high homology with the intM, dot-blot hybridization was then conducted using the intM of N315 as primers with respect to the following standard strains of various Staphylococcus strains: ATCC25923, NCTC8325 (*S. aureus*), ATCC14990 (*S. epidermidis*), ATCC29970 (*S. haemolyticus*), DSM20672 (*S. arlettae*), CCM3573 (*S. caprae*), ATCC29062 (*S. sciuri*), ATCC33753 (*S. auricularis*), ATCC27840 (*S. capitis*), DSM20501 (*S. carnosus*), ATCC29750 (*S. caseolyticus*), NCTC10530 (*S. chromogenes*), ATCC29974 (*S. cohnii*), DSM20771 (*S. delphini*), DSM20674 (*S. equorum*), JCM7469 (*S. felis*), CCM3572 (*S. gallinarum*), ATCC27844 (*S. hominis*), ATCC29663 (*S. intermedius*), DMS20676 (*S. kloosii*), ATCC29070 (*S. lentus*), ATCC43809 (*S. lugdunensis*), ATCC15305 (*S. saprophyticus*), ATCC43808 (*S. schleiferi subsp. schleiferi*), JCM7470 (*S. schleiferi subsp. coagulans*), ATCC27848 (*S. simulans*), ATCC27836 (*S. warneri*), and ATCC29971 (*S. xylosus*). As a result, 9) The probes of the intM did not undergo hybridization with the standard strain of any strain other than *Staphylococcus aureus*.

From the foregoing results, the following conclusions have been obtained:

1) There are at least three types of mec DNAs in MRSA strains. They are different from each other in most regions, but two (N315mec and NCTC10442mec) of them have homologous sequences in downstream ends of their mec DNAs (FIG. 12).

2) At the both ends of mec there are relatively-retained IRs of 20–30 nucleotides.

3) In all the MRSA strains studied, the integration sites of the mec DNAs in the chromosomes of the MRSA strains are the same, that is, are located in the intMs (FIGS. 17, 18, 19).

4) The nucleotide sequences of the intMs are substantially the same at least on right sides (in downstream regions) relative to the downstream junctions of the mec region DNAs (FIG. 6).

5) The nucleotide sequences of the region upstream from the 5' end of the intMs are the same in the three types of MRSA strains (FIGS. 13, 15, 15, 18 and 19).

6) Between the type-2 and type-4 coagulase strains, their nucleotide sequences are different on the 3' sides (left sides) of the intMs relative to the mec integration sites (FIG. 6).

By using the nucleotide sequences of mec, intM and a 5'-side region thereof on the basis of these findings, it is possible to conduct identification of MRSA strains by various methods to be described hereinafter. Although a description will hereinafter be made of a concept of a method in which primers or probes are used surrounding a downstream junction of a mec, similar effects can also be obtained from surrounding an upstream junction of the mec. However, the latter method which is performed surrounding the upstream junction of the mec requires to design a set of primers or probes of at least N315, NCTC10442 and 85/3907 on the basis of the nucleotide sequences of these three strains including the upstream junctions of the mec region DNAs. For the selection of the primers or probes in this case, designing and combinations of numerous primers are feasible surrounding the upstream junctions of the mec region DNAs from PSJ8-2a (the nucleotide sequences of FIGS. 9 and 10), L02C4 (the nucleotide sequences of FIG. 12), LG12H2 (the nucleotide sequence of FIG. 16) and the nucleotide sequence of FIG. 5.

Figure 7:
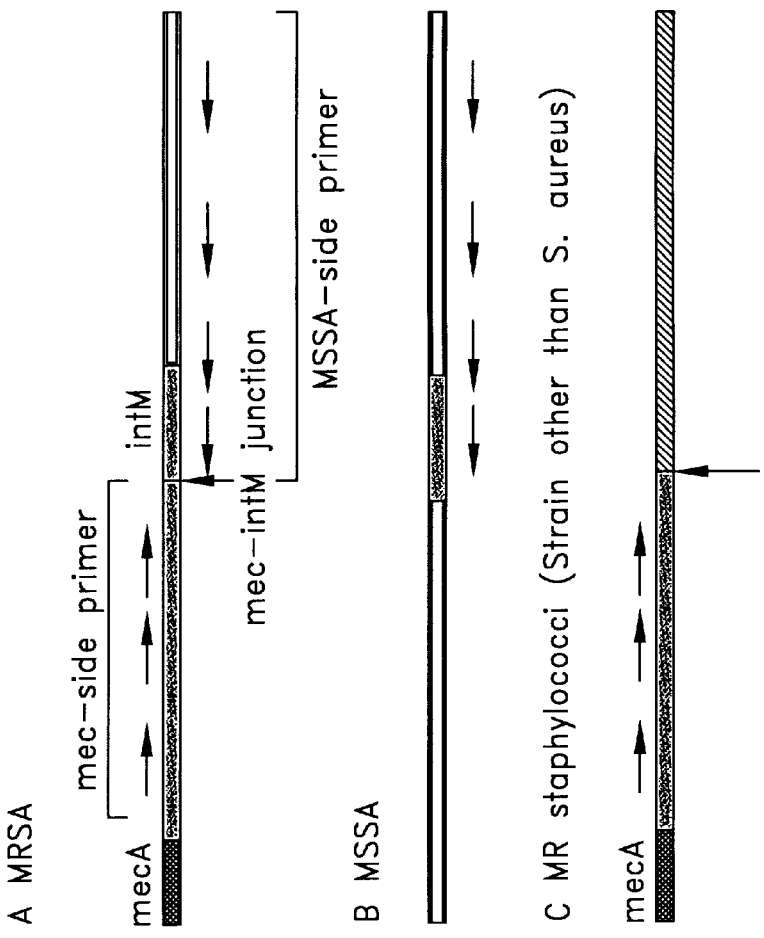
FIG. 7 is a diagram illustrating an outline of an MRSA identification method. Arrow marks indicate primers for PCR. With a chromosomal DNA of MSSA, the primers set as in A react of the MSSA-side primers but do not react at the mec-side primers (B). Further, with a chromosomal DNA of a Staphylococcus strain other than mec-carrying *S. aureus,* the mec-side primers react but the MSSA-side primers do not react (C).

Identification method of MRSA by setting primers or probes which surround a downstream junction of mec (1) Primers are designed in a mec region DNA and at intM and its 5'-side, and PCR is used. As is illustrated in FIG. 7, a strain is determined to be an MRSA if a DNA fragment containing a junction between the mec and the intM is amplified (FIG. 7A). In the case of an MSSA, a negative reaction is shown because the primer on the side of the mec region DNA cannot react (FIG. 7B). Concerning a mec region DNA containing strain other than *Staphylococcus aureus,* a negative reaction is also shown as no reaction is feasible with the primer at the intM and its 5'-side (FIG. 7C).

(2) When LCR (ligase chain reaction) is relied upon, an MRSA can be identified by preparing two DNA fragments, surrounding the junction between the mec and the intM, and then conducting a reaction.

(3) An MRSA can be identified by synthesizing a single or double-strand DNA probes, including the junction between the mec and the intM, and then using hybridization.

(4) By the above methods, many MSSA-side primers or probes can be chosen from the nucleotide sequence pLEC12 of the intM and its surrounding chromosome region (the nucleotide sequence of FIG. 4) and also from the nucleotide sequences of the intM and its 5'-side in the nucleotide sequence of FIG. 5.

(5) Many mec-side primers or probes can be chosen from nucleotide sequences corresponding to mec region DNAs in the following nucleotide sequences, namely, N315IS-J3 (the nucleotide sequence of FIG. 17), NCTC10442J3rc (the nucleotide sequence of FIG. 18) and pSJ10-3J3rc (the nucleotide sequence of FIG. 19).

(6) An MRSA or MSSA can be identified by extracting an RNA from cells of the MRSA, MSSA or the like, converting it into a DNA with a reverse transcriptase, and conducting PCR, LCR or hybridization while using the above-described primers or probes.

(7) An MRSA or MSSA can also be identified by extracting an RNA from cells and then amplifying it in accordance with nucleic acid sequence-based amplification (NASBA) (Jean Compton: *Nature* 350, 91–92, 1991) in which three enzymes (RNaseH, AMV-RT, T7RNA polymerase) and two primers are reacted at the same time.

According to these methods, the existence of an MRSA can be directly confirmed without going through culture of the strain from a patient's sample even if a mec-containing Staphylococcus strain other than *Staphylococcus aureus* is mixed. Accordingly these methods are useful as fast diagnostic methods and have high value in clinical diagnoses.

Figure 8:
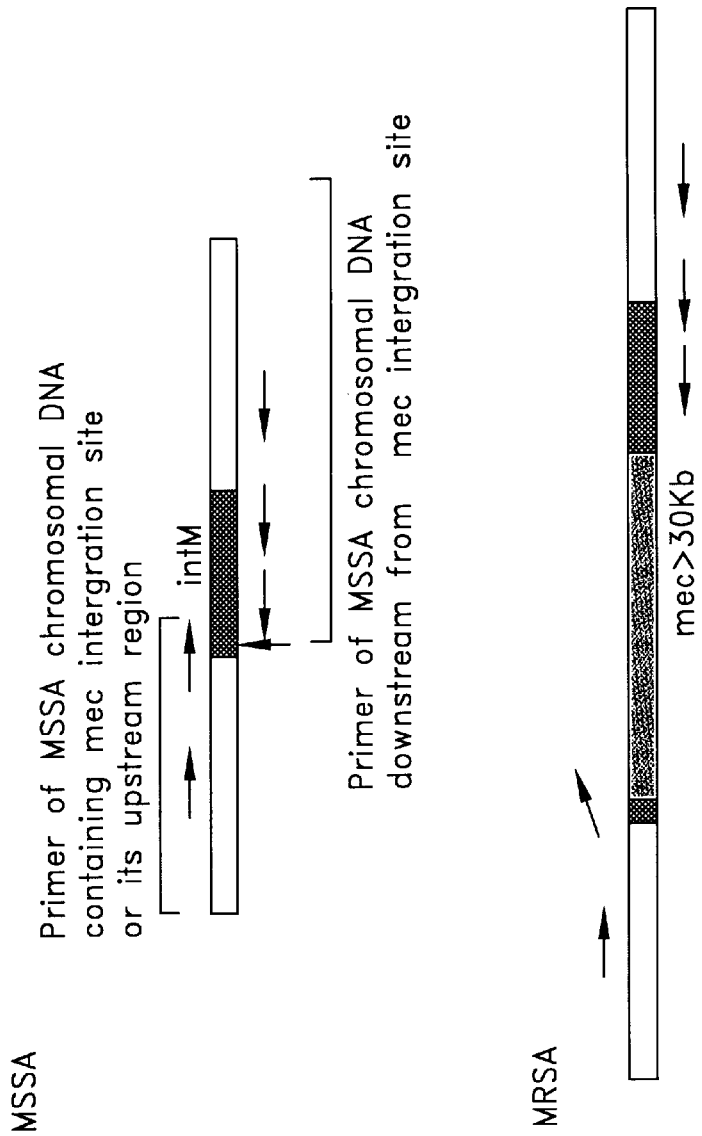
FIG. 8 is a diagram illustrating a concept of an internal control in PCR. When primers are designed in such a way as surrounding an intM-containing region of MSSA, they react with the chromosomal DNA of MSSA so that the DNA fragment is amplified by PCR. In the case of the chromosomal DNA of MRSA, on the other hand, no amplification is feasible by usual PCR because of the integration of a mec DNA greater than 30 Kb. Further, when primers are synthesized including a mec integration site, these primers themselves no longer react in the case of MRSA.

Further, if as a negative control for an identification method of an MRSA, a primer or probe is designed including a 3'-side region of intM relative to a mec integration site or the integration site as shown in FIG. 8 and PCR or NASBA is performed, a negative result is obtained if a strain is an MRSA or a positive result is obtained if the strain is an MSSA. The primer or probe therefore makes it possible to conduct evaluation of diagnosis conditions as an internal negative control. It is also possible to perform identification of an MRSA by making use of the fact that PCR or NASBA gives a negative result in this method. However, a patient's sample with an MSSA mixed therein gives a positive result in these tests. It is therefore desired to perform this method in addition to the above-described method (1), (2), (3), (6) or (7) after isolation and culture of a strain determined as an MRSA. Numerous primers or probes or combinations thereof, which are usable for these purposes, can be chosen from nucleotide sequences corresponding to MSSA chromosomal DNAs containing or surrounding mec integration sites of the following nucleotide sequences: pLEC12 (pLEC1a) (the nucleotide sequence of FIG. 4), pSJ8-2a (the nucleotide sequence of FIGS. 9 and 10), L02C4 (the nucleotide sequence of FIG. 12) and LG12H2 (the nucleotide sequence of FIG. 16).

When the above methods (1) to (7) were performed with respect to 28 epidemic MRSA strains in 18 countries, including Japan, of the world, positive results were obtained in all the tests. However, negative results were obtained from MSSA strains, standard strains of Staphylococcus strains other than *Staphylococcus aureus* and mec-containing clinical Staphylococcus strains other than *Staphylococcus aureus,* all of which were employed as controls. This has substantiated that this diagnostic method is extremely effective and useful (Table 1).

TABLE 1

Specific Identification of MRSAS by
PCR, Surrounding mec-intM Junction

| Strain | Probe (J6 + Nmec5 + Gmec1045a) | |
|---|---|---|
| | Negative | Positive |
| MSSAs - 11 strains* | 11 | 0 |
| MRSAs - 26 strains** | 0 | 26 |
| Standard Staphylococcus strains - 25 strains*** | 25 | 0 |
| MR Staphylococcus strains including MRC-NS - 20 strains**** | 20 | 0 |

*Japanese clinical strains including the three standard strains, ATCC25923, NCTC8325 and ATCC12600.
**Epidemic strains in 18 countries: England, NCTC10442, 61/6219, 61/3846, 61/4176, 86/4372, 86/560, 86/961, 86/2652, 86/9302; Yugoslavia, 85/1340; Hungary, 85/1762; New Zealand, 85/2082; Norway, 85/2111; Holland, 85/3566; Saudi Arabia, 85/5495; Japan, MR108, N315; South Africa, 84/9580; Germany (West), 85/1836; France, 85/1940; Hong Kong, 85/2147; Austria, 85/3619; Germany (East), 85/3907; Canada, 85/4231, 85/4670; Israel, 85/4547; U.S.A., 85/2232, 85/2235.
***Standard Staphylococcus strains other than *Staphylococcus aureus*: ATCC14990 (*S. epidermidis*), ATCC29970 (*S. haemolyticus*), DSM20672 (*S. arlettae*), CCM3573 (*S. caprae*), ATCC29062 (*S. sciuri*), ATCC33753 (*S. auricularis*), ATCC27840 (*S. capitis*), DSM20501 (*S. carnosus*), ATCC29750 (*S. caseolyticus*), NCTC10530 (*S. chromogenes*), ATCC29974 (*S. cohnii*), DSM20771 (*S. delphini*), DSM20674 (*S. equorum*), JCM7469 (*S. felis*), CCM3572 (*S. fallinarum*), ATCC27844 (*S. hominis*), ATCC2963 (*S. intermedius*), DMS20676 (*S. kloosii*), ATCC29070 (*S. lentus*), ATCC43809 (*S. lugeunensis*), ATCC15305 (*S. saprophyticus*), ATCC43808 (*S. schleiferi* subsp. *schleiferi*), JCM7470 (*S. schleiferi* subsp. *coagulans*), ATCC27848 (*S. simulans*), ATCC27836 (*S. warnerii*), and ATCC29971 (*S. xylosus*).
****Methicillin-resistant clinical Staphylococcus strains other than *Staphylococcus aureus*: *S. haemolyticus*, 10 strains; *S. epidermidis*, 10 strains; *S. sciuri*, 3 strains; *S. caprae*, 2 strains; *S. hominis*, 2 strains; *S. capitis*, 1 strain; *S. warnerii*, 1 strain.

Specific Detection Method of MRC-NS

A mec region DNA similar to that integrated in an MRSA is also integrated in an MRC-NS. However, the nucleotide sequence of a chromosomal DNA around the mec integration site is different from the corresponding sequence in the MRSA and is a nucleotide sequence specific to the C-NS strain. By using this finding, specific detection of the MRC-NS is possible by combining the nucleotide sequence surrounding the mec integration site and the nucleotide sequence of the mec. Similarly to the above-described specific detection method of the MRSA, the MRC-NS can also be specifically detected by using a method such as PCR, LCR, hybridization, RT-PCR or NASBA.

The present invention will hereinafter be described in more detail by setting out examples in each of which a DNA fragment containing mec and a mec-integration site is cloned from an MRSA strain, examples in each of which a DNA fragment containing a mec integration site is cloned from an MSSA strain, and the like. It is however to be noted that the present invention shall not be limited only to them.

EXAMPLE 1

Cloning of DNA fragments (two fragments, i.e., upstream and downstream fragments), which contain a mec region DNA (mec) and a junction sequence between the mec and an MSSA chromosomal DNA, from N315 strain; and cloning of a chromosomal DNA fragment, which contains a mec integration site (int), from an MSSA standard strain NCTC8325

1) Among Japanese MRSAs in the 1990s, type-2 coagulase and TSST-1 producing strains account for more than 70% throughout Japan [Tae Tanaka et al. *J. Infect. Chemother.* 1(1), 40–49, 1995]. An MRSA clinical strain N315 (Keiichi Hiramatsu et al., *FEBS Lett.* 298, 133–136, 1991), which is identical in coagulase type and ribotype to those epidemic MRSAs (Keiichi Hiramatsu, *Nihon Rinsho* 50, 333–339, 1992), was cultured overnight in L-broth and was then suspended in 10 mM Tris, 1 mM EDTA (pH 8.0). After lysed by achromopeptidase treatment, proteinase K treatment was conducted. Extraction was conducted with phenol and then with chloroform, whereby a chromosomal DNA was extracted. Using the chromosomal DNA so extracted, a plasmid library and a λ phage (λ dash II) library were prepared.

Described specifically, the chromosomal DNA was cleaved by a restriction endonuclease Sau3A I. Fragments as large as from 9 Kb to 20 Kb were purified by agarose gel electrophoresis and were then used. In the case of the plasmid library, 0.3 μg of the Sau3A I fragment and 1.1 μg of a plasmid vector pACYC184, which had been cleaved by a restriction endonuclease BamH I, were subjected to ligation, followed by transformation of an *E. coli* strain MC1061. A target clone was then obtained by colony hybridization. In the case of the phage library, 0.3 μg of the Sau3A I fragment and 1 μg of λdash II, which had been cleaved by BamH I, were subjected to ligation. In vitro packaging was then conducted. After infected to an *E. coli* strain XL1-blue MRA(P2), colony hybridization was conducted, whereby a target clone was obtained. Concerning probes to be employed in the hybridization, the mecA was used as a first probe. The next probe was then prepared by synthesis of oligonucleotide or by subcloning after determining the nucleotide sequences of DNA fragments of end regions of resultant DNAs. Further, clones containing adjacent DNA regions were successively cloned (chromosome walking) (FIG. 1).

2) In this manner, starting from a clone pSJ1 containing the mecA gene, pSJ2, pSJ4, pSJ5, pSJ7 and pSJ8 were obtained. These clones were individually subjected to subcloning, whereby probes 1, 2, 3, 4, 5, 6, 7, 8, 9, 10 and 11 were obtained. Using these probes, the reactivity of each probe was studied by dot-blot hybridization while employing chromosomal DNAs extracted from 29 MRSA strains and 9 MSSA strains. Namely, with respect to each of the chromosomal DNA, 200 ng of the chromosomal DNA were subjected to heat treatment at 95° C. for 5 minutes and were then spotted on nylon membrane. Subsequent to a reaction with each probe which had been conjugated with digoxigenin, a further reaction was conducted with an anti-digoxigenin antibody conjugated with alkaline phosphatase, followed by the addition of a luminous substrate AMPPD to perform detection. As a result, the probes 1 to 9 did not react at all with the MSSA strains, and it was the probe 10 that reactions with the MSSA strains took place for the first time. From these results, the probe 10 was found to be a DNA fragment containing the upstream junction of the mec.

3) In accordance with dideoxy termination, the nucleotide sequence of the probe 10 was determined using an autosequencer (Applied biosystem 373A). Sequence reactions were conducted using a DyeDeoxy Terminator Cycle Sequencing Kit and a Dye Primer Cycle Sequencing Kit.

4) Next, to specify a chromosomal DNA region containing the integration site of the mec, cloning of a chromosomal DNA fragment of an MSSA was performed using a DNA probe 11 for a region reactive with the MSSA at the upstream end of the mec (FIG. 1). A chromosomal DNA extracted from NCTC8325 was cleaved by the restriction endonuclease Sau3A I. After 0.3 µg of DNA fragment of from 9 kb to 20 kb, which had been prepared by agarose gel electrophoresis, and 1 µg of λ dash II cleaved by BamH I were subjected to ligation, packaging was performed to prepare a phage library. From plaques showed positive result in plaque hybridization, a recombinant phage was then recovered.

5) By dot-blot hybridization, a DNA clone LD8325 subcloned from the above-described recombinant phage was found to undergo hybridization with the probe 10. Subsequent to preparation of a restriction map, subcloning of an EcoR I-Pst I fragment (pLE1a) containing the integration site of the mec was therefore performed to determine its nucleotide sequence.

6) As a result of the nucleotide sequence comparison between the subclone pLE1a (pLEC12 reverse complementary) of LD8325 and the nucleotide sequence of the probe 10 (pSJ8-2a), these nucleotide sequences showed high mutual homology on left side relative to the mec integration sties (FIGS. 9 and 10).

7) Employing as a probe, a DNA fragment (probe N1) amplified by PCR while using primers J4 and a Nif, which was set on a right side relative to the mec integration site in LD8325, a genomic library of N315 was next subjected to screening by plaque hybridization, whereby a DNA clone LN4 containing a downstream junction of N315 mec was obtained.

8) As a result of determination of the nucleotide sequence of LN4 subclone pLN2 (J3 reverse complementary) containing the mec integration site, the nucleotide sequence of the subclone on an outer side relative to the mec integration site was found to be substantially the same as that of the intM and its upstream region (5' side) (see FIG. 4) of LD8325 (pLEC12 reverse complementary) (FIG. 11). As has been described above, the mec of N315 was found to be integrated at a certain particular site on the MSSA chromosome.

EXAMPLE 2

Using the MRSA clinical strain NCTC10442 reported in England for the first time in the world (Jevons, M. P. *Br. Med. J.* 1, 124–125, 1961) as an epidemic MRSA strain isolated outside Japan, a chromosomal DNA containing mec and its integration site was cloned. Namely, 1) Using procedures similar to those employed above in the case of N315, clones L02, L05 and L07 containing the mec and its upstream junction were cloned (FIG. 2), and their nucleotide sequences were determined.

2) As a result of a sequence comparison between the subclone L02C4 containing the upstream junction of the mec and the pSJ8-2a of N315, a region corresponding to the outside of the junction on the MSSA chromosome was found to be homologous with pSJ8-2a although the nucleotide sequence of the upstream end of the mec was substantially different (FIG. 12).

3) Using the probe N1, the phage library of NCTC10442 was thus subjected to screening by plaque hybridization, whereby the clone L021 containing the downstream junction of the mec was obtained and its nucleotide sequence was determined.

4) As is shown in FIG. 13, a sequence common to NCTC10442 and N315 was observed in a region with corresponded to the downstream from the mec junction on MSSA chromosome In their nucleotide sequences of downstream end regions in the mec region DNAs, however, no homology was observed except for the sequences of IRs.

5) However, in a region approximately 200 nucleotides preceding toward the upstream side from the mec junction in NCTC10442, a nucleotide sequence homologous to the downstream end region of the mec in N315 was found (FIG. 14).

6) From the foregoing, it has been found that the mec region DNAs of the two MRSA strains are integrated at the same integration site although they are considerably apart from each other geologically and in time, that is, they were found in Japan and England and in 1982 and 1961, respectively and moreover, they are different in epidemiological markers such as coagulase type; and further that a nucleotide sequence common to both the MRSA strains can be observed although the structures inside their mec region DNAs are different.

7) On the other hand, the structures of mec region DNAs are however diverse. It is therefore necessary to adequately perform designing of effective primers based on the concept and procedures disclosed in the present invention after determination of the structure and nucleotide sequence of each mec with respect to epidemic MRSA strains spread over the world.

EXAMPLE 3

Concerning epidemic MRSA strains isolated outside Japan, a structural analysis of their mec region DNAs was conducted accordingly. Epidemic MRSA strains most widely spread over the various countries of the world are MRSAs of the coagulase type 4 [Keiichi Hiramatsu: Microbiol. Immunol. 39(8), 531–543, 1995]. Using the German strain 85/3907 which is a typical example of these MRSAs, a chromosomal DNA fragment containing mec and its junctions was cloned (FIG. 3).

1) Using the probe 11 and the probe N1, the plasmid library of the chromosomal DNA of 85/3907 was subjected to screening by colony hybridization, whereby reactive two clones pSJ9 and pSJ10 were obtained.

2) The nucleotide sequences of these clones were determined. The clone pSJ10 contained a nucleotide sequence identical to intM, and in registration with the med integration sites in N315 and NCTC10442, homologous base sequences were observed in the nucleotide sequences of the downstream end regions of the mec region DNAs in these MRSA strains. However, the nucleotide sequence of the downstream end region of the mec in 85/3907 was different from those of N315 and NCTC10442 (FIG. 15).

3) The nucleotide sequence of the other clone pSJ9 (FIG. 3) did not contain any mec junction site.

4) Using the phage library of 85/3907, a DNA fragment reactive with the clone pSJ9 was therefore subjected to cloning by plaque hybridization. In addition, a clone LG12 was obtained by using the nucleotide sequence of the DNA fragment ends as probe. A similar operation was then repeated to perform chromosome walking (FIG. 3).

5) None of these reacted with the chromosomal DNA of NCTC 10442, and MSSA strain, by dot-blot hybridization.

6) Accordingly, the chromosomal DNA of ATCC25923, which is a standard MSSA strain of the coagulase type 4, was extracted, and its dot-blot hybridization with the above-described clones was performed. The hybridization gave positive results. Hybridization, however, gave a negative result when the right-side part of the clone LG12 out of the above-described clones was used as a probe.

7) As a result of determination of the nucleotide sequence LG12H2 of LG12, practically no homology was observed both inside and outside the mec except for the observation of sequences homologous to the IR nucleotide sequences of the upstream ends of the mec region DNAs and approximately 20 bases located adjacent to the junctions and corresponding to the 3' end regions of intMs in N315 and NCTC10442 (FIG. 16).

8) From the foregoing, it has been found that there are MRSA strains of clearly different origins, which occurred as a result of integration of the mec into the chromosomes of different MSSAs, and that at least the MSSA chromosome region on the outer side (left side) of the upstream junction of the mec significantly differs among the MRSA strains of different origins.

9) Nonetheless, the MSSA chromosome region, including the nucleotide sequence of the intM, was reserved on the outer side (right side) of the downstream junction of the mec as far as all the MRSA strains investigated were concerned.

10) Upon designing primers or probes surrounding mec junctions for use in PCR, LCR or hybridization, it has been found that PCR requires to design different mec-side base sequences, one for N315 and NCTC10442 and another for 85/3907. When LCR or hybridization is relied upon, three primers or probes have to be prepared for N315, NCTC10442 and 85/3907, respectively.

11) As has been described above, it has become apparent that identification of an MRSA by PCR, LCR or hybridization around the mec-MSSA chromosome junction cannot be practiced if the initial finding, which teaches merely that the mec has the same chromosome integration site on chromosomal DNA of some MRSAs [Keiichi Hiramatsu: Microbiol. Immunol. 39(8), 531–543, 1995], is solely relied upon.

EXAMPLE 4

Verification of homology of the mec in MRSAs

1) Using as probes DNA clones covering the respective mec regions of N315, NCTC10442 and 85/3907, their reactivity with the chromosomal DNAs of 26 epidemic MRSA strains isolated in 18 countries of the world was screened by dot-blot hybridization. After 100 ng/μl of a chromosomal DNA solution and T10E1 (10 mM Tris, 1 mM EDTA [pH 8.0]) were mixed in equal amounts, the resulting mixture was heated for 95° C. for 5 minutes. The mixture was allowed to cool down, to which 20×SSC was added in an equal amount. Then, 4 μl of the thus-prepared mixture was spotted on nylon membrane. Subsequent to denaturation with 0.5 N NaOH and 1.5 M NaCl, neutralization was conducted with 1.5 M Tris (pH 7.3), 1.5 M NaCl and 1 mM EDTA. Using the probes conjugated with digoxigenin, hybridization was conducted. Detection was performed using an anti-digoxigenin antibody conjugated with alkaline phosphatase.

2) As is presented in Tables 2, 3 and 4, the above-described three mec region DNAs have been found to be practically undetectable by their corresponding probes.

3) It has been suggested that the use of the respective mec probes of N315, NCTC10442 and 85/3907 makes it possible to classify the 26 strains into any one of the above-described three types (Tables 2, 3 and 4).

TABLE 2

Distribution of the mec of
N315 Strain among MRSA strains

| | | Probe[1] | | | | | | | | | | | | | | |
|---|---|---|---|---|---|---|---|---|---|---|---|---|---|---|---|---|
| | | | | | | | | | | | | | mecR1 | | | |
| | Strain[2] | 11 | 10 | 9 | 8 | 7 | 6 | 5 | 4 | 3 | 2 | 1 | mecI | PB | MS | mecA | 12 |
| II | N315 | + | + | + | + | + | + | + | + | + | + | + | + | + | + | + | + |
| III | 10443 | + | + | − | − | − | − | − | − | + | + | + | − | − | + | + | + |
| | 61/6291 | + | + | − | − | − | − | − | − | + | ±[3] | − | − | − | + | + | NT[4] |
| | 64/3846 | + | + | − | − | − | − | − | − | + | ± | − | − | − | + | + | NT |
| | 64/4176 | + | + | − | − | − | − | − | − | + | + | ± | − | − | + | + | NT |
| | 86/4372 | + | + | − | − | − | − | + | + | + | + | − | − | + | + | NT |
| IV | 86/961 | + | − | − | − | − | − | − | − | + | + | + | + | + | + | + | NT |
| | 86/560 | + | − | − | − | − | − | − | − | + | + | + | + | + | + | + | NT |
| | 85/1340 | + | − | − | − | − | − | − | − | + | + | + | + | + | + | + | + |
| | 85/1762 | + | − | − | − | − | − | − | − | + | + | + | + | + | + | + | NT |
| | 85/2082 | + | − | − | − | − | − | − | − | + | + | + | + | + | + | + | NT |
| | 85/2111 | + | − | − | − | − | − | − | − | + | + | ± | + | + | + | + | NT |
| | 85/1836 | + | + | − | − | − | − | − | − | + | + | + | + | + | + | + | NT |
| | 85/2147 | + | − | − | − | − | − | − | − | + | + | + | + | + | + | + | NT |
| | 86/3907 | + | − | − | − | − | − | − | − | + | + | + | + | + | + | + | NT |
| | 86/2652 | + | − | − | − | − | − | − | − | + | + | + | + | + | + | + | NT |
| | 85/5495 | + | − | − | − | − | − | − | − | + | + | + | + | + | + | + | NT |
| | 85/3619 | + | − | − | − | − | − | − | − | + | + | + | + | + | + | + | NT |
| | 85/3566 | + | − | − | − | − | − | − | − | + | + | + | + | + | + | + | NT |

TABLE 2-continued

Distribution of the mec of
N315 Strain among MRSA strains

| | | Probe[1] | | | | | | | | | | | | mecR1 | | | |
|---|---|---|---|---|---|---|---|---|---|---|---|---|---|---|---|---|---|
| | Strain[2] | 11 | 10 | 9 | 8 | 7 | 6 | 5 | 4 | 3 | 2 | 1 | mecI | PB | MS | mecA | 12 |
| II | 85/2235 | + | + | + | + | + | + | + | + | + | + | + | + | + | + | + | NT |
| | 84/9580 | + | + | – | – | – | – | – | + | + | + | – | – | – | + | + | NT |
| | 86/9302 | + | + | – | – | – | – | – | + | + | + | ± | – | – | + | + | NT |
| | 85/1940 | + | – | – | – | – | + | ± | + | + | ± | – | – | + | + | NT |
| IV | 85/4231 | + | + | + | + | + | + | + | + | + | + | ± | + | + | + | + | NT |
| | 85/2232 | + | + | + | + | + | + | + | + | + | + | + | + | + | + | + | NT |
| VII | 85/4547 | + | – | – | – | – | – | – | + | + | – | – | – | – | + | + | NT |

[1]PB, penicillin-binding domain; MS, membrane-spanning domain.
[2]Roman numbers indicate coagulase types.
[3]Weak positive signal.
[4]Not tested.

TABLE 3

Distribution of the mec of
NCTC10442 Strain among MRSA strains

| | | Probe[1] | | | | | | | | mecR1 | | |
|---|---|---|---|---|---|---|---|---|---|---|---|---|
| | Strain[2] | 7 | 6 | 5 | 4 | 3 | 2 | 1 | mecI | PB | MS | mecA |
| II | N315 | – | – | – | – | – | – | – | + | + | + | + |
| III | 10442 | + | + | + | + | + | + | + | – | – | + | + |
| | 61/6291 | + | + | + | + | + | + | + | – | – | + | + |
| | 64/3846 | + | + | + | + | + | + | + | – | – | + | + |
| | 64/4176 | + | + | + | + | + | + | + | – | – | + | + |
| | 86/4372 | + | – | – | – | – | – | ±[3] | – | – | + | + |
| IV | 86/961 | – | – | – | – | – | – | ± | + | + | + | + |
| | 86/560 | – | – | – | – | – | – | – | + | + | + | + |
| | 85/1340 | – | – | – | – | – | – | – | + | + | + | + |
| | 85/1762 | – | – | + | – | – | – | + | + | + | + | + |
| | 85/2082 | – | – | + | – | – | – | + | + | + | + | + |
| | 85/2111 | – | – | – | – | – | – | – | + | + | + | + |
| | 85/1836 | – | – | – | – | – | – | – | + | + | + | + |
| | 85/2147 | – | – | – | – | – | – | – | + | + | + | + |
| | 85/3907 | – | – | – | – | – | – | – | + | + | + | + |
| | 86/2652 | – | – | ± | – | – | – | ± | + | + | + | + |
| | 85/5495 | – | – | ± | – | – | – | – | + | + | + | + |
| | 85/3619 | ± | – | + | – | – | – | ± | + | + | + | + |
| | 85/3566 | – | – | ± | – | – | – | – | + | + | + | + |
| II | 85/2235 | ± | – | + | – | – | – | ± | + | + | + | + |
| | 84/9580 | + | + | + | + | + | + | + | – | – | + | + |
| | 86/9302 | + | + | + | + | + | + | + | – | – | + | + |
| | 85/1940 | + | + | + | + | + | + | + | – | – | + | + |
| IV | 85/4231 | – | – | – | – | – | – | – | + | + | + | + |
| | 85/2232 | – | – | – | – | – | – | – | + | + | + | + |
| VII | 85/4547 | – | – | + | + | – | – | + | – | – | + | + |

[1]PB, penicillin-binding domain; MS, membrane-spanning domain.
[2]Roman numbers indicate coagulase types.
[3]Weak positive signal.

TABLE 4

Distribution of the mec of
85/3907 Strain among MRSA strains

| | | Probe[1] | | | | | | | | mecR1 | | |
|---|---|---|---|---|---|---|---|---|---|---|---|---|
| | Strain[2] | 7 | 6 | 5 | 4 | 3 | 2 | 1 | mecI | PB | MS | mecA |
| II | N315 | − | − | − | − | ±[3] | − | − | + | + | + | + |
| III | 10442 | − | − | − | − | − | − | − | − | − | + | + |
| | 61/6291 | − | − | ± | − | − | − | − | − | − | + | + |
| | 64/3846 | − | − | ± | − | − | − | − | − | − | + | + |
| | 64/4176 | − | − | − | − | + | + | − | − | − | + | + |
| | 86/4372 | − | − | − | − | − | − | − | − | − | + | + |
| IV | 86/961 | + | ± | + | + | + | + | + | + | + | + | + |
| | 86/560 | + | ± | + | + | + | + | + | + | + | + | + |
| | 85/1340 | + | ± | + | + | ± | + | + | + | + | + | + |
| | 85/1762 | + | + | + | + | + | + | + | + | + | + | + |
| | 85/2082 | + | + | + | + | + | + | ± | + | + | + | + |
| | 85/2111 | + | + | + | + | + | + | + | + | + | + | + |
| | 85/1836 | + | + | + | + | + | + | + | + | + | + | + |
| | 85/2147 | + | + | + | + | ± | + | + | + | + | + | + |
| | 85/3907 | + | + | + | + | + | + | + | + | + | + | + |
| | 86/2652 | + | ± | + | + | + | + | + | + | + | + | + |
| | 85/5495 | + | ± | + | − | ± | + | ± | + | + | + | + |
| | 85/3619 | + | + | + | + | + | + | + | + | + | + | + |
| | 85/3566 | + | + | + | + | + | + | + | + | + | + | + |
| II | 85/2235 | − | − | + | − | + | + | − | + | + | + | + |
| | 84/9580 | ± | − | ± | − | ± | + | − | − | − | + | + |
| | 86/9302 | − | − | − | − | − | − | − | − | − | + | + |
| | 85/1940 | − | − | − | − | ± | − | − | − | − | + | + |
| IV | 85/4231 | + | − | ± | − | + | + | − | + | + | + | + |
| | 85/2232 | + | − | ± | − | ± | + | − | + | + | + | + |
| VII | 85/4547 | − | − | + | + | − | − | + | − | − | + | + |

[1]PB, penicillin-binding domain; MS, membrane-spanning domain.
[2]Roman numbers indicate coagulase types.
[3]Weak positive signal.

EXAMPLE 5

Based on the base sequences of the mec region DNAs of N315 and NCTC10442, probes for the detection of the mec region DNAs of types 2j and 3e were synthesized by a method known per se in the art. Nucleotide sequences for the selection of primers were designed based on N315IS-J3 (FIG. 17) and NCTC10442J3rc (FIG. 18), which is a nucleotide sequence of a mec region extending from IS431 (FIG. 1) on the right side of (downstream from) the mec to the downstream junction in N315. The followings are primers chosen as desired. Similar primers can be designed in a large number on the basis of the above-described nucleotide sequences. The nucleotide sequences of the primers will be shown next together with their positions as indicated by nucleotide numbers in N315IS-J3 (FIG. 17).

EXAMPLE 6

Based on the nucleotide sequence pSJ10-3J3rc (FIG. 19) of the mec of 85/3907, a probe for the detection of the mec of type 4e was synthesized.

Gmec1045 5'-ATATTCTAGATCATCAATAGTTG-3' 10-33 (SEQ ID NO:24)

EXAMPLE 7

Based on the base sequence pLEC12 (pLEC1a) (FIG. 4) of the intM and its upstream region, primers for the detection of the chromosomal DNAs of MSSAs were synthesized.

```
Nmec2    5'-GATAGACTAATTATCTTCATC-3'       229–249    (SEQ ID NO:18)

Nmec3    5'-CAGACTGTGGACAAACTGATT-3'      507–527    (SEQ ID NO:19)

Nmec4    5'-TGAGATCATCTACATCTTTA-3'       676–695    (SEQ ID NO:20)

Nmec4-2  5'-GGATCAAAAGCTACTAAATC-3'       903–922    (SEQ ID NO:21)

Nmec5    5'-ATGCTCTTTGTTTTGCAGCA-3'       1504–1523  (SEQ ID NO:22)

Nmec6    5'-ATGAAAGACTGCGGAGGCTAACT-3'    2051–2073  (SEQ ID NO:23)
```

```
J3      5'-AAGAATTGAACCAACGCATGA-3'              1664-1684 (SEQ ID NO:25)

intM1   5'-AAACGACATGAAAATCACCAT-'               1389-1409 (SEQ ID NO:26)

J7      5'-TCGGGCATAAATGTCAGGAAAAT-3'            1267-1289 (SEQ ID NO:27)

J6      5'-GTTCAAGCCCAGAAGCGATGT-3'               949-969  (SEQ ID NO:28)

Nif     5'-TTATTAGGTAAACCAGCAGTAAGTGAACAACCA-3'  639-671   (SEQ ID NO:29)
```

EXAMPLE 8

Preliminary Experiment for the PCR Detection of MRSA by Combination of Primers Constructed on mecDNA and Downstream Region to mecDNA.

A preliminary experiment for the setting of primers was conducted by combining 6 primers prepared based on the nucleotide sequences of the mec region DNAs of N315 and NCTC10443 for the detection of the mec region DNAs of types 2j and 3e, 2 primers prepared based on the nucleotide sequence of the mec region DNAs of 85/3907 for the detection of the mec region DNAs of type 4e, and 6 primers prepared based on the nucleotide sequence of the intM and its upstream region for the detection of the chromosome DNAs of MSSAs. PCR was performed in 20 µl to 50 µl of reaction mixtures [10 mM Tris-HCl pH 8.3, 50 mM KCl, 1.5 mM MgCl$_2$, 0.001%(w/v) gelatin, 200 µM dNTPs, 1.0 µM primer, template DNA, 0.01 u/µl Taq DNA polymerase). As reaction conditions, a system in which 94° C.-30 sec, 55° C.-1 min and 72° C.-2 min was repeated 30 cycles was used. As PCR, "GeneAmp PCR System 9600" (Parkin Elmer) was used. For the detection of each PCR product, 5 µl of the reaction mixture were applied to electrophoresis through a 0.8% agarose gel after completion of the reaction. Subsequent to the electrophoresis, staining was conducted for 30 minutes in a 0.1 M aqueous solution of ethidium bromide, followed by the detection of bands on a transilluminator.

RESULTS 1

As is shown in Table 5, the epidemic MRSA strains in various countries of the world, which were subjected to the test, were all classified into one of two types, one being reactive with Gmec1045 prepared based on the nucleotide sequences of the mec region DNAs of N315 and NCTC10442, and the other reactive with Nmec6 prepared based on the nucleotide sequence of the mec region DNA of 85/3907. It has therefore been indicated that use of primers prepared based on the nucleotide sequences of the above-described two types of mec region DNAs makes it possible to detect and identify all the MRSAs in the various countries of the world.

TABLE 5

| Strain | | Combination of primers | |
|---|---|---|---|
| | | J7-Nmec6 | J7-Gmec1045 |
| 82/N315 | Japan | + | − |
| 85/2235 | U.S.A. | + | − |
| 84/9580 | Germany | + | − |
| 86/9302 | U.K. | + | − |
| 85/1940 | France | + | − |
| 10442 | U.K. | + | − |

TABLE 5-continued

| Strain | | Combination of primers | |
|---|---|---|---|
| | | J7-Nmec6 | J7-Gmec1045 |
| 61/6219 | U.K. | + | − |
| 64/3846 | U.K. | + | − |
| 986/4372 | U.K. | + | − |
| 86/961 | U.K. | + | + |
| 86/560 | U.K. | + | + |
| 85/1340 | Yugoslavia | − | + |
| 85/1762 | Hungary | − | + |
| 85/2082 | New Zealand | − | + |
| 85/2111 | Norway | − | + |
| 85/1836 | Germany | − | + |
| 85/3907 | Germany | − | + |
| 86/2652 | England | − | + |
| 85/5495 | Saudi Arabia | − | + |
| 85/3619 | Austria | − | + |
| 85/3566 | Holland | − | + |
| 85/4231 | Canada | + | − |
| 85/2232 | U.S.A. | + | − |
| 85/4547 | Israel | + | − |

RESULTS 2

Concerning primers, Nmec2, 3, 4, 4-2, 5 and 6 were used as mecDNA primers, and J7, Nif and J6 were employed as downstream primers of the mec-integrated regions. In the combinations with the primers of the Nmec series, J7, J6 and Nif all indicated positive reactions. Strong signals were observed especially when J6 or J7 was used. In an experiment of combinations between Gmec1045 and MSSA-side primers, a strong signal was obtained from each combination.

Described specifically, in the combinations of J7 and the mecDNA primers Nmec2, 3, 4, 4-2, 5 and 6, bands of 2500, 2300, 2100, 1900, 1300 and 700 bp of PCR products were observed, respectively, on agarose electrophoresis. In the combinations of Nif and the mecDNA primers Nmec2, 3, 4, 4-2, 5 and 6, bands of 3200, 2900, 2700, 2500, 1900 and 1400 bp were observed, respectively. Further, in the combinations of J6 and the mecDNA primers Nmec2, 3, 4, 4-2, 5 and 6, bands of 2800, 2600, 2400, 2200, 1600 and 1000 bp were observed, respectively.

In an experiment in which the DNA of the MRSA strain 85/3907 was used, PCR products were not amplified in any of the above combinations, and PCR products were detected when Gmec1045 was used as a mecDNA primer. Namely, in combinations of Gmec1045 and Nif, J6, J7, intM1 or J3 as downstream primers of the mec-integrated region, bands of 1300, 1000, 700, 600 and 300 bp were detected, respectively, by electrophoresis.

EXAMPLE 9
Experiment for Setting a Primer Combination Suited for Mixing

An investigation was next conducted concerning mixing of two mec primers and one MSSA-side primer. Conditions for PCR were similar to those employed in Example 8. To detect all MRSAs by a single operation of PCR, one of J7, Nif and J6 was used as a downstream primer of a mec-integrated region, and as mecDNA primers, the mecDNA primer Gmec1045 reactive with the mecDNA of 85/3907 and one of the mecDNA primers, Nmec2, 3, 4, 4-2, 5 and 6, reactive with mecDNAs of the N315 and NCTC10442 type were chosen. These three types of primers were mixed. Using the DNAs of N315 and 85/3907 as templates, amplification was performed by PCR to determine a combination which would lead to detection of a product in a largest quantity.

RESULTS

When the primers of the Nmec series were combined with the individual combinations of Gmec1045 with J7, Nif and J6, the use of Gmec1045 and J6 gave good signals except that signals became somewhat weaker when Nmec4, 3 and 2 primers were added. When Nmec6, 5 and 4-2 were used in combination with the same combination, signals were rather stronger that those available from the other combinations.

Described specifically, when the DNA of N315 was used as a template, each of the combinations of J7, Gmec1045 and (Nmec2, 3, 4, 4-2, 5 and 6) led to clear detection of a PCR product upon staining an agarose gel with ethidium bromide. In the combinations of Nif, Gmec1045 and (Nmec2, 3, 4, 4-2, 5 and 6), on the other hand, strong bands were detected from the use of Nmec5 and 6 primers. However, bands were weak in the case of Nmec3, 4 and 4-3 primers. No band was detected when Nmec2 was used. Further, in the combinations of J6, Gmec1045 and (Nmec2, 3, 4, 4-2, 5 and 6), a weak band was detected in the case of Nmec6, no bands were detected in the case of Nmec2, 3 and 4, and strong bands were detected in the case of Nmec4-2 and 5. With Nmec5 in particular, a strongest band was confirmed out of those obtained from all the combinations. From the foregoing, it has been substantiated that sufficient results cannot be obtained in certain combinations of primers and careful optimization is hence important. From these results, the combination of J6, Gmec1045 and Nmec5 has been found to be an optimal primer combination.

EXAMPLE 10
Investigation on Specificity of Detection Method of MRSA by PCR

Based on the results of Example 9, the effectiveness of the primer combination of J6, Gmec1045 and Nmec5 was investigated in accordance with PCR by using MRSAs, MSSAs and clinical staphylococcus strains other than *Staphylococcus aureus*, said clinical staphylococcus strains including both those containing mec and those carrying no mec. PCR reactions were performed using a templates the DNAs of 26 MRSA clinical strains, 11 MSSA strains, 25 standard c-NS strains and 20 MRC-NS clinical strains. As a primer, the three primers J6, Gmec1045 and Nmec5 were used as a mixture. The primer was the mixture of the following three primers, and Gmec1045 and Nmec5 were used on the mec side while J6 was employed on the MSSA side. PCR was performed in 20 µl to 50 µl of reaction mixtures [10 mM Tris-HCl pH 8.3, 50 mM KCl, 1.5 mM MgCl$_2$, 0.001%(w/v) gelatin, 200 µM dNTPs, 1.0 µM primer, template DNA, 0.01 u/µl Taq DNA polymerase]. As reaction conditions, a system in which 94° C.-30 sec, 55° C.-1 min and 72° C.-2 min were repeated 30 cycles was used.

It is Table 1 that summarizes the results of the above investigation. The MRSAs in the various countries of the world all showed positive signals, whereas the MSSAs all indicated negative results. The staphylococcus strains other than *Staphylococcus aureus* all gave negative results no matter whether or not they had mec.

Namely, clear bands were detected from all the MRSA strains. Concerning their sizes, there were bands of 1.6 kb (N315 type) from 8 strains, bands of 1.5 kb (NCTC10442 type) from 5 strains, and bands of 1 kb (85/3907 type) from 13 strains. From these results, it has been indicated that MRSAs can be all detected and can be classified into three types in accordance with the size of amplified DNA fragments. From each of the MSSA strains, C-NS strains and MRC-NS strains, no band was detected at all. Accordingly, MRSA specificity of this detection method has been demonstrated.

EXAMPLE 11
Specific Detection of MRSA by RT-PCR

Using MRSA, MRC-NS and MSSA clinical strains, the whole RNAs of the individual strains were extracted and then converted into DNAs by RT-PCR, and genes were screened. Employed as primers for detection were Nmec4-2, Nmec5 and Nmec6 in Example 5, Gmec1045 used in Example 6 and IntM1 in Example 7.

Used as clinical strains were: as MSSA(mec-) strains, ATCC25923 strain and NCTC8325 strain; as MRSA(mec+) strains, N315 strain, NCTC10442 strain and 85/3907 strain; and as MRC-NS strains, the *S. haemolyticus* strains SH518 and SH631 and the *S. epidermidis* strain G13.

Each strain was cultured overnight in LB medium. The resultant cells were collected by centrifugation, washed with PBS, suspended in a 1 ml RNase-free PK/SDS solution [200 µg/ml, Proteinase K, 0.5% SDS, 10 mM Tris-HCl, pH 8.0 1 mM EDTA (pH 8.0), 100 mM NaCl], and then incubated at 55° C. for 60 minutes. Extraction was next performed with phenol/chloroform/isoamyl alcohol (50/49/1) and further with chl/IAA (49/1), followed by precipitation in ethanol. The resulting pellet was rinsed with 75% ethanol and, after dried in air, was dissolved with 20 µl nuclease-free water. The whole RNAs obtained as described above were treated with DNase (37° C., 60 min). After completion of the reaction, DNase was inactivated. Then, extraction was performed with phl/chl/IAA and then with chl/IAA, followed by precipitation in ethanol. The resulting pellet was dissolved with 10 µl of nuclease-free water. Next, the thus-obtained whole RNAs were heated at 95° C. for 2 minutes and then quenched on ice. RT buffer (20 µl/sample) was added and reverse transcription was conducted, whereby cDNA was obtained. Subsequent to reaction at 25° C. for 10 minutes, at 37° C. for 60 minutes, and then at 90° C. for 5 minutes in a thermal cycler ("TAKARA MP TP3000"), a PCR reaction was performed in a manner known per se in the art.

For the specific detection of MRSA by PCR, it is necessary to combine a primer for N315 and NCTC10442 and a primer for 85/3907 as a forward primer. First, #393(Nmec5) and #347(Gmec1045) were used for the detection of MRSA. Similarly, #210(jun1) and #351(25923-1) were combined as a primer for the detection of MSSA. For the reverse side, #212(jun3) was used out of the primers within the intM. Incidentally, the distance from jun3 primer to the mec integration site is 193 bp, including the primer (21 mer).

| Primer name | Concentration (pmol/µl) | Target (strain) |
|---|---|---|
| (1) #210 Junction 1(jun1) | 82.1 | MSSA(NCTC8325) |
| (2) #260 10442-J-3-1(Nmec6) | 92.0 | MRSA(N315,NCTC10442) |
| (3) #330 1S431-right 7-2(Nmec4-2) | 138.4 | MRSA(N315,NCTC10442) |
| (4) #347 pSJ10-4-5(Gmec1045) | 67.9 | MRSA(85/3907) |
| (5) #351 25923-1 | 266.8 | MSSA(ATCC25923) |
| (6) #393 1S431-right 5-new(Nmec5) | 128.6 | MRSA(N315,NCTC10442) |

Reaction conditions for PCR were as described below, and two forward primers were employed. Concerning the amount of the template, a portion (1 µl) of an RT reaction mixture, which is equivalent to 50 ng as calculated from the total RNA amount (1 µg/20 µl) at the time of initiation of the RT reaction, was taken and then added to a PCR reaction system of 50 µl.

<PCR reaction mixture [MRSA]>

| Contents | Volume/ sample | Final conc. |
|---|---|---|
| Water (nuclease-free, SIGMA) | 42.4 µl | — |
| 10x PCR buffer (with MgCl$_2$, TAKARA)* | 5.0 µl | 1x |
| 20 mM dNTPs (TAKARA) | 0.5 µl | 200 µM |
| Forward primer | | |
| 67.9 µM Gmec1045 | 0.4 µl | 540 nM |
| 128.6 µM Nmec5 | 0.2 µl | 510 nM |
| 84.3 µM reverse primer jun3 | 0.3 µl | 510 nM |
| 5 U/µl Taq DNA polymerase (TAKARA) | 0.2 µl | 1U/50 µl |
| RT product (cDNA; template) | 1.0 µl | — |
| Total | 50.0 µl | |

<PCR reaction mixture [MSSA]>

| Contents | Volume/ sample | Final conc. |
|---|---|---|
| Water (nuclease-free, SIGMA) | 42.6 µl | — |
| 10x PCR buffer (with MgCl$_2$, TAKARA)* | 5.0 µl | 1x |
| 20 mM dNTPs (TAKARA) | 0.5 µl | 200 µM |
| Forward primer | | |
| 82.1 µM jun1 | 0.3 µl | 490 nM |
| 266.8 µM 25923-1 | 0.1 µl | 530 nM |
| 84.3 µM reverse primer jun3 | 0.3 µl | 510 nM |
| 5 U/µl Taq DNA polymerase (TAKARA) | 0.2 µl | 1U/50 µl |
| RT product (cDNA; template) | 1.0 µl | — |
| Total | 50.0 µl | |

*10x PCR buffer: 100 mM Tris-HCl (pH 8.3), 500 mM KCl, 15 mM MgCl$_2$

After the reaction mixture other than the template was prepared and mixed, it was poured in 49 µl portions into 0.5 ml PCR tubes in each of which 50 µl of light liquid paraffin (TOYOBO) had been placed in advance. Finally, the below-described templates were added in amounts of 1 µl, respectively. Each of the resulting mixtures was agitated with tapping, and after being flushed down, the mixture was set in the "Thermal Cycler MP" to initiate a PCR reaction. As a negative control for the PCR, water was used. On the other hand, plasmid pLEC1a DNA (about 500 ng/µl) was diluted 100-fold in water, and 1 µl (about 5 ng) of the dilute solution was used as a positive control for MSSA-PCR.

| Template | RTase | Template | RTase |
|---|---|---|---|
| (1) ATCC25923 (MSSA) | − | (7) NCTC10442 (MRSA) | − |
| (2) ATCC25923 (MSSA) | + | (8) NCTC10442 (MRSA) | + |
| (3) NCTC8325 (MSSA) | − | (9) 85/3907 (MRSA) | − |
| (4) NCTC8325 (MSSA) | + | (10) 85/3907 (MRSA) | + |
| (5) N315 (MRSA) | − | (11) Water (PCR negative control) | |
| (6) N315 (MRSA) | + | (12) pLEC1a (PCR positive control) | |
| Denaturation | | at 94° C. for 30 sec. | |
| Primer annealing | | at 50° C. for 1 min. | |
| Chain elongation (extension) | | at 72° C. for 2 min. | |

After the reaction was repeated 30 cycles at the above reaction temperatures, the amplified product was reserved at 4° C. until it was subjected to electrophoresis.

Confirmation of amplified products

With respect to the amplified products obtained by the PCR, their confirmation was performed by electrophoresis in a 2% agarose gel. The gel was prepared by adding 2% of agarose ("SeaKem GTG agarose, FMC) to 0.5× TBE (44.5 mM Tris, 44.5 mM borate, 1 mM EDTA), dissolving the resultant mixture and then processing the thus-prepared solution in a gel maker of a submarine-type small electrophoresis apparatus (Mupid-COSMOBIO). From the amplified products (50 µl), 10 µl which were equivalent to one fifth of the amplified products were taken. Subsequent to the addition of 2 µl of a dye (0.25% bromophenol blue, 0.25% xylene cyanol FF, 1 mM EDTA, 30% glycerol), the amplified products were applied to a well and then subjected to electrophoresis at 100 V for 45 minutes in 0.5× TBE buffer. As a size marker, 100 bp DNA Ladder (100–1500 bp+2072 bp, 1 µg/µl, GIBCO BRL) was used in an amount of 0.5 µl. After the electrophoresis, the gel was immersed in TBE buffer containing 0.5 µg/ml of ethidium bromide, and was stained at room temperature for 20 minutes. Then, the amplified fragments were confirmed on a UV transilluminater and also photographed by a Polaroid camera (Polaroid MP4/type 667 film).

As a result of electrophoresis of a portion of the amplified products in an 2% agarose gel, no amplified products were confirmed in the case of the RTase-free templates in both of the MRSA and MSSA detection PCRs. mRNA-origin amplified products were confirmed only in the presence of RTase. Accordingly, the thus-obtained amplified products were all confirmed to be cDNA-origin ones synthesized from mRNA by reverse transcription. In the MRSA detection PCR, no amplified products were confirmed in the case of the two MSSA strains, and those of different lengths [N315(906 bp)>NCTC10442(804 bp)>85/3907(361 bp) were obtained in the case of the three MRSA strains. In the MSSA detection PCR, on the other hand, no amplified products were confirmed in the case of MRSAs, and amplified products of different lengths (AGTC25923>NCTC8325) were obtained only in the case of the two MSSA strains. Further, in the case of the PCR positive control (pLEC1a), amplified products were observed only in the MSSA detection PCR so that amplified products as large as NCTC8325, the source for pLEC1a, were obtained.

From the above results, it has been confirmed that mRNA of a mec region, which is needed for the specific detection of MRSA, is not observed in the case of MSSA but is developed only in the case of MRSA.

EXAMPLE 12

Specific Detection of MRSA by NASBA

Using MRSA, MRC-NS and MSSA clinical strains, the whole RNAs of the individual strains were extracted. RNAs were then amplified by NASBA. Amplification primers and detection probes were designed as will be described hereinafter.

As forward primers

N315(MRSA), 5'-GAAAGAGGCGGAGGCTAA-3' (SEQ ID NO:30)
NCTC10442

85/3907    5'-CATCTAAACATCGTATGA-3' (SEQ ID NO:31)

As reverse primers
As a probe for detecting of the intM region

3'-AAACGGGAACCCAGTACGCA-promotor-5' (SEQ ID NO:32)

of each strain, reverse primers were designed commonly to the individual strains on the basis of the base sequence of the intM region.

Designed were:
For capturing

5'-GCTGAATGATAGTGCGTAGTTAC-3' (A) (SEQ ID NO:33)

For detection

5'-TGAAGACGTCCTTGTGCA-3' (B); or (SEQ ID NO:34)

For capturing

5'-TGAATGATAGTGCGTAGTTACTGCG-3' (C) (SEQ ID NO:35)

For detection

5'-TCATTTGATGTGGGAATGTG-3' (D) (SEQ ID NO:36)

Used as clinical strains were: as MSSA(mec–) strains, ATCC25923 strain and NCTC8325 strain; as MRSA(mec+) strains, N315 strain, NCTC10442 strain and 85/3907 strain; and as MRC-NS strains, the S. haemolyticus strains SH518 and SH631 and the S. epidermidis strain G13.

Each strain was cultured overnight in LB medium. From the resultant cells, the whole RNAs were collected in a similar manner as in Example 11. After samples were prepared by subjecting the RNAs to 10-serial dilution (1 pg/µl to 1 µg/µl) in water, the following NASBA-dot hybridization was conducted.

1. Elution
   1) Each sample (0.5 ml) is placed in an eluent buffer tube and is stirred several times.
   2) The tube is centrifuged (1,500×g, 15 seconds).

2. Separation
   1) A control solution (system control solution, 20 µl) is added to the tube, followed by centrifugation.
   2) A silica suspension (70 µl) is added to each tube, is allowed to stand at room temperature (15 to 30° C.) for 10 minutes, and is then stirred intervals of 2 minutes.
   3) Each tube is centrifuged (1,500×g, 2 minutes).
   4) The supernatant is thrown away.
   5) After silica particles are re-suspended, centrifugation is conducted and the supernatant is removed. The residue is washed with a wash buffer, with 70% ethanol (2 twice), and then with acetone (4 times). Centrifugation is performed.
   6) The resulting silica pellet is dried (56° C., 10 minutes).

7) An eluate (100 μl) is added for re-suspension. The resultant suspension is stirred (56° C., 10 minutes) to elute nucleic acids.

8) Centrifugation is performed (10,000×g, 2 minutes).

3. Amplification

1) A primer (15 μl) is added to 8 μl of the nucleic acid supernatant. After a reaction at 65° C. for 5 minutes, the reaction mixture is cooled at 41° C. for at least 5 minutes.

2) An enzyme solution (2 μl) is added, and a reaction is allowed to proceed (41° C., at least 5 minutes).

3) The tube is moved into a detection compartment. The mixture is gently stirred, followed by a reaction at 41° C. for 90 minutes.

4. Detection

1) The reaction mixture of 3-3) is diluted approximately 10-fold, 1 μl of the dilute solution is dropped on a Hybound N+blotting membrane (Amersham), and the membrane is placed for 5 minutes on a piece of filter paper soaked with 0.6 N NaOH. The membrane is washed and neutralized with a 5x SSC solution. On a piece of filter paper, water was removed. The membrane is heated at 50° C. for 15 minutes in a hybridization buffer under shaking, and then placed in a probe solution formed of 1 ml of a hybridization buffer and 1 μl of an ALP probe added thereto, where the membrane is heated at 50° C. for 15 minutes under shaking. The membrane is moved into a 2XSSC/1% SDS solution and heated at 50° C. for 15 minutes under shaking. At room temperature, the membrane is heated for 15 minutes in 1XSSC/0.5% Triton X and then for 5 minutes in a 1XSSC solution under shaking. The membrane is then reacted with a staining solution at 37° C. for 10 to 60 minutes. After the membrane is washed under shaking in purified water, water is removed on a piece of filter paper and dried to observe staining. The results are showed in Table 6.

TABLE 6

| Staphylococcus aureus | Probe A (for capturing) Probe B (for detection) | Probe B (for capturing) Probe A (for detection) |
| --- | --- | --- |
| MSSA | | |
| 1) ATCC25923 | − | ± |
| 2) NCTC8325 | − | − |
| MRSA | | |
| 1) N315 | + | + |
| 2) NCTC10442 | + | + |
| 3) 85/3907 | + | + |
| MRS-NS | | |
| 1) S. haemolyticus SH518 | − | − |
| 2) S. epidermidis G3 | − | − |

+: clear color production,
±: unclear color production, and
−: color production was not detected.

EXAMPLE 13

Specific Detection of Methicillin-Resistant
S. haemolyticus by PCR

A primer intMh was prepared based on the specific base sequence of the region on the right side of the mec-integrated region (the region downstream from the mecA) in MR S. haemolyticus of FIG. 6 intMh: 5'-GATCAAATGGATTGCATGAGGA-3'(SEQ ID NO: 37)

(corresponding to the base numbers 236 to 260 in FIG. 6).

When PCR reactions were conducted by combining this primer with the mec-specific primers in Example 5, bands of 2100, 1800, 1700, 1400, 850 and 300 bp were detected, respectively, from the combinations with Nmec2, Nmec3, Nmec4, Nmec4-2, Nmec5 and Nmec6 in the case of 10 methicillin-resistant S. haemolyticus strains such as SH518 and SH631. However, bands were not detected at all in the case of MRSAs, MSSAs, standard strains of methicillin-susceptible C-NSs, and clinical strains.

EXAMPLE 14

Specific Detection of Methicillin-Resistant
S. epidermidis by PCR

A primer intMe was prepared based on the specific nucleotide sequence of the region on the right side of the mec-integrated region (the region downstream from the mecA) in MR S. epidermidis of FIG. 6.

intMe: 5'-TCTTCAGAAGGACTCGCTAA-3'(SEQ ID NO: 38)

(corresponding to the base numbers 318 to 337 in FIG. 6)

When PCR reactions were conducted by combining this primer with the mec-specific primers in Example 5, bands of 2200, 1900, 1800, 1600, 900 and 400 bp were detected, respectively, from the combinations with Nmec2, Nmec3, Nmec4, Nmec4-2, Nmec5 and Nmec6 in the case of 10 methicillin-resistant S. epidermidis strains such as G3. However, bands were not detected at all in the case of MRSAs, MSSAs, standard strains of methicillin-susceptible C-NSs, and clinical strains.

From the foregoing, it has been substantiated that, when two primers are synthesized at the downstream end of mec and a further primer is synthesized within intM or on its 5' side, most of mec region DNAs of primary MRSA clinical strains in the world can be detected and also that this method does not give any false positive result even if one or more of wide-spread human staphylococci other than mec-carrying Staphylococcus aureus are mixed.

Capability of Exploitation in Industry

When conditions for super high-speed identification of MRSA and MRC-NS from a clinical sample are set by using the present method, MRSA can be detected directly from a sample such as sputum, blood, urine or exudate in 30 minutes to 1 hour within scope of the conventionally-known art. This method makes it possible to perform bedside identification of MRSA from a patient's sample, thereby permitting selection of an effective chemotherapeutic agent and early treatment of MRSA and NRC-NS infectious diseases. Further, this method is also useful as a test for the prevention of outbreak of nosocomial infection, because it can also be applied for the MRSA carrier screening of normal subjects such as those engaged in medical work.

What is claimed is:

1. A method of identifying a methicillin-resistant *Staphylococcus aureus* (MRSA) or a methicillin-resistant coagulase-negative staphylococci (MRC-NS) present, if any, in a biological sample, which comprises the steps of:

bringing the biological sample in contact with (a) an oligonucleotide having a nucleic acid sequence specific to a MRSA or MRC-NS to be detected, said nucleic acid sequence included in a mecDNA which is an integrated adventitious DNA existing on a chromosome of said MRSA or MRC-NS and carrying a mecA gene, mecRI/mecI genes, an IS431 insertion element, and inverted repeats at its 5' and 3' ends thereon, and (b) an oligonucleotide having a nucleic acid sequence included in an IntM chromosomal DNA surrounding said mecDNA to form a reaction product of the biological sample and oligonucleotides (a) and (b); and identifying the MRSA or MRC-NS by detecting said reaction product.

2. A method according to claim 1, wherein the contacting step further comprises performing a polymerase chain reaction (PCR) using oligonucleotides (a) and (b) as primers to amplify a DNA fragment containing sequences between said mecDNA and the chromosomal DNA flanking said mecDNA of the MRSA or MRC-NS, and wherein said identifying step comprises detecting the presence or absence of a PCR product.

3. A method according to claim 1, wherein the contacting step further comprises performing a ligase chain reaction (LCR) using oligonucleotides (a) and (b) as primers to amplify the region between said mecDNA and said chromosomal DNA surrounding said mecDNA, and wherein said identifying step comprises detecting the presence or absence of an LCR product.

4. A method according to claim 1, wherein the contacting step further comprises performing hybridization using a single- or double-strand DNA fragment as a probe which surrounds junctions between said mecDNA and said chromosomal DNA surrounding said mecDNA, wherein said hybridization is between said single- or double-strand DNA fragment and a DNA of the MRSA or MRC-NS, and wherein said identifying step comprises detecting the presence or absence of hybridization.

5. A method according to claim 1, wherein said mecDNA has an upstream end region having a nucleic acid sequence selected from the group consisting of: pSJ8-2a listed as SEQ ID NO:1, L02C4 listed as SEQ ID NO:2, LG12H2 listed as SEQ ID NO:3, a nucleotide sequence which has the inverse complement of the foregoing, and a nucleotide sequence having substantially the same specificity to the MRSA or MRC-NS as the foregoing.

6. A method according to Claim 1, wherein said mecDNA has a downstream end region having a nucleic acid sequence selected from the group consisting of: N315IS-J3 listed as SEQ ID NO:4, NCTC10442J3rc listed as SEQ ID NO:5, pSJ10-3J3rc listed as SEQ ID NO:6, a nucleotide sequence which has the inverse complement of the foregoing, and a nucleotide sequence having substantially the same specificity to the MRSA or MRC-NS as the foregoing.

7. A method according to Claim 1, wherein said nucleotide sequence of said chromosomal DNA surrounding said mecDNA is selected from the group consisting of:
pLEC12(pLEC1a) listed as SEQ ID NO:7,
N315J3rc listed as SEQ ID NO:8;
NCTC10442J3rc listed as SEQ ID NO:5;
pSJ10-3J3rc listed as SEQ ID NO:6;
the nucleotide sequence listed as SEQ ID NOs:9–13;
the nucleotide sequence listed as SEQ ID NOs:14–17;
pSJ8-2a listed as SEQ ID NO:1;
L02C4 listed as SEQ ID NO:2;
LG12H2 listed as SEQ ID NO:3;
a nucleotide sequence which has the inverse complement of the foregoing, and
a nucleotide sequence having substantially the same specificity to the MRSA or MRC-NS as the foregoing.

8. A method of identifying an MRSA or MRC-NS present, if any, in a biological sample, by PCR, LCR or hybridization, which comprises the steps of:
bringing the biological sample in contact with an oligonucleotide or multiple oligonucleotides wherein one oligonucleotide comprises a nucleic acid sequence of an IntM chromosomal DNA surrounding an integration site of a mecDNA in MRSA or MRC-NS, to form a reaction product, said mecDNA being an integrated adventitious DNA existing on a chromosome of a methicillin-susceptible *Staphylococcus aureus* or methicillin-susceptible C-NS and carrying a mecA gene, mecRI/mecI genes, and IS431 insertion element, and inverted repeats at its 5' and 3' ends; and
identifying the MRSA or MRC-NS by detecting the absence of a reaction product due to integration of said mecDNA.

9. A method according to claim 8, wherein, in the contacting step, two oligonucleotides containing said integration site of the mecDNA or surrounding said integration site of the mecDNA are used in PCR and, in the identifying step, positive identification of MRSA or MRC-NS occurs when there is no amplification of said DNA fragment by PCR due to integration of said mecDNA.

10. A method according to claim 8, wherein, in the contacting step, two oligonucleotides containing said integration site of the mecDNA or surrounding said integration site of the mecDNA are used in LCR, and, in the identifying step, positive identification of MRSA or MRC-NS occurs when there is no amplification of DNA fragments by LCR due to integration of said mecDNA.

11. A method according to claim 8, wherein, in the contacting step, a single- or double-strand DNA fragment is prepared using said oligonucleotide to produce a probe by PCR or LCR, said probe containing said integration site of the mecDNA, and wherein in the identifying step, positive identification of MRSA or MRC-NS occurs when there is no hybridization.

12. A method according to claim 8, wherein said integration site of the mecDNA or surrounding said integration site of the mecDNA has a nucleic acid sequence selected from the group consisting of:
pLEC12(pLEC1a) listed as SEQ ID NO:7,
pSJ8-2a listed as SEQ ID NO:1;
L02C4 listed as SEQ ID NO:2;
LG12H2 listed as SEQ ID NO:3;
the nucleotide sequences listed as SEQ ID NOs:9–13;
the nucleotide sequences listed as SEQ ID NOs:14–17;
a nucleotide sequence which has the inverse complement of the foregoing, and
a nucleotide sequence having substantially the same specificity to the MRSA or MRC-NS as the foregoing.

13. A method according to claim 1, wherein said biological sample comprises a DNA obtained by reverse transcription of staphylococcus RNA.

14. A method according to claim 1, wherein said biological sample comprises an RNA obtained by nucleic acid sequence-based amplification (NASBA).

15. A method according to claim 8, wherein said biological sample comprises a DNA obtained by reverse transcription of staphylococcus RNA.

16. A method according to claim 8, wherein said biological sample comprises an RNA obtained by NASBA.

* * * * *